US007204814B2

(12) United States Patent
Peles

(10) Patent No.: US 7,204,814 B2
(45) Date of Patent: Apr. 17, 2007

(54) ORTHODYNAMIC REHABILITATOR

(75) Inventor: Zalman Peles, Kfar Korazim (IL)

(73) Assignee: Muscle Tech Ltd., Htzrim (IL)

( * ) Notice: Subject to any disclaimer, the term of this patent is extended or adjusted under 35 U.S.C. 154(b) by 77 days.

(21) Appl. No.: 10/446,808

(22) Filed: May 29, 2003

(65) Prior Publication Data

US 2004/0243025 A1    Dec. 2, 2004

(51) Int. Cl.
*A61H 1/00* (2006.01)
*A61H 1/02* (2006.01)

(52) U.S. Cl. ............................................ 601/5; 601/33
(58) Field of Classification Search .................... 601/5, 601/33, 34, 35, 40
See application file for complete search history.

(56) References Cited

U.S. PATENT DOCUMENTS

| | | | |
|---|---|---|---|
| 4,558,692 A | 12/1985 | Greiner | |
| 4,601,468 A | 7/1986 | Bond et al. | |
| 4,697,808 A | 10/1987 | Larson et al. | |
| 4,711,450 A | 12/1987 | McArthur | |
| 4,828,257 A * | 5/1989 | Dyer et al. | 482/5 |
| 4,885,939 A | 12/1989 | Martin | |
| 5,078,152 A * | 1/1992 | Bond et al. | 601/33 |
| 5,121,747 A | 6/1992 | Andrews | |
| 5,211,161 A * | 5/1993 | Stef | 601/5 |
| 5,252,102 A | 10/1993 | Singer et al. | |
| 5,399,147 A * | 3/1995 | Kaiser | 601/34 |
| 5,466,213 A | 11/1995 | Hogan et al. | |
| 5,662,693 A | 9/1997 | Johnson et al. | |
| 5,961,541 A | 10/1999 | Ferrati | |
| 6,035,274 A | 3/2000 | Kramer et al. | |
| 6,109,852 A | 8/2000 | Shahinpoor et al. | |
| 6,221,032 B1 | 4/2001 | Blanchard et al. | |
| 6,244,873 B1 | 6/2001 | Hill et al. | |
| 6,267,735 B1 | 7/2001 | Blanchard et al. | |
| 6,379,393 B1 | 4/2002 | Mavroidis et al. | |
| 6,450,922 B1 * | 9/2002 | Henderson et al. | 482/8 |
| 2004/0102723 A1 * | 5/2004 | Horst | 601/5 |

OTHER PUBLICATIONS

Optiflex S—Under Manual (Chattanooga Group Inc) Medtrade 2002.
http://www.asel.udel.edu/ rocotics/newsletter/showcase12.html, Jan. 15, 1998.

* cited by examiner

*Primary Examiner*—Danton DeMille
(74) *Attorney, Agent, or Firm*—Lilling & Lilling PLLC; Bruce E. Lilling; Sean Liam Kelleher

(57) ABSTRACT

The present invention is a portable orthotic system that performs predefined or user-controlled limb movements, collects data regarding limb movement, performs data analysis and displays representations of the data and data analysis results in real time, and modifies current operational parameters based upon such data so as to optimize the rehabilitative process performed by the system.

54 Claims, 23 Drawing Sheets

120

122

124

| | Position | Max. Force | 0-5 Scale |
|---|---|---|---|
| Elbow | Inner | | |
| | Middle | | |
| | Outer | | |
| Forearm | Position | Max. Force | 0-5 Scale |
| | Inner | | |
| | Middle | | |
| | Outer | | |

Classical muscle testing -

FIG. 14

ORTHODYNAMIC REHABILITATOR

FIELD AND BACKGROUND OF THE INVENTION

The present invention relates to orthotic devices and, in particular, it concerns an orthotic system that operates in either a rehabilitative mode or an assistive mode.

It is known in the field of rehabilitative medicine that providing range of motion to partially and/or fully non-functional limbs prevents muscle atrophy. Range of motion exercises after surgery are known to decrease post-operative pain and swelling.

Historically, movement of the limb was provided "hands on" by a therapist. In recent years, however, the hands of the therapists are being replaced by rehabilitative orthotic devices, the most popular currently appears to be the group on devices referred to as "continuous passive motion" (CPM) machines. While the CPMs relieve the therapist from the mundane job of moving a limb repeatedly through a prescribed range of motion, the machines lack the human hands-on feel of the nuances of how the limb's response to the movement. The lack of sensitivity of the part of CPM machines also creates a situation wherein the limb may be even further damaged by the continuation of movement if an emergency, such as resistance to the movement, occurs. The challenge has become finding ways for machines to collect and implement data with similar results to the "hands-on" data collected implemented mentally by a therapist.

A number of CPM devices have been developed that use resistance to the movement of the device to trigger a modification of the devices movement. These modifications, however, are based only attaining a preset threshold of resistance to movement, and are generally stopping or reversing direction of the actuating member of the device, or a combination of the two. U.S. Pat. No. 4,558,692 to Greiner describes a device that includes an override switch that, if resistance is encountered, will automatically stop and reverse the motor to prevent injury or discomfort to the patient. The Optiflex®, marketed by Chattanooga Group, Inc., utilizes a similar safety feature.

Another attempt to humanize CPM devices is disclosed in U.S. Pat. No. 6,267,735 to Blanchard et al. The Blanchard et al. device is a continuous passive motion device that may be programmed to stop and reverse the direction of its carriage when a patient activates a "Comfort Zone" feature upon experiencing discomfort (luring flexion or extension. The device may be programmed to establish a reduced range of motion or Comfort Zone for a number of cycles of flexion and extension, after which the range of motion will preferably be gradually and automatically increased or advanced until flexion and/or extension may be carried out at the point at Which discomfort was experienced. The preferred embodiment of the Blanchard et al. device thus provides the patient with immediate relief from discomfort while allowing flexion and extension to continue automatically and in a controlled manner until flexion and/or extension may be carried out at the point at which discomfort was experienced. In this way, the preferred embodiment of the Blanchard et al. device provides a CPM device which may be operated so as to decrease the likelihood that the patient will experience similar discomfort when the carriage returns to the point along the axis of the frame at which discomfort was initially experienced (and at which the Comfort Zone feature was actuated). The human element, however, is just that, and while the Blanchard et al. device allows a wider range of human input to the operational parameters of the machine, it does not provide information relating to the bodies response to therapy other than discomfort zones.

The above referenced CPM machines are characterized as being for therapeutic rehabilitation use. The Motorized Upper Limb Orthotic System (MULOS) developed by the Centre for Rehabilitation and Engineering Studies (CREST), University of Newcastle upon Tyne, UK, is a device that can operate in a CPM mode or an assistive mode. In its assistive mode, the device is controlled by a joystick so as to direct the movement of the limb. The MULOS is also a very large device that is mounted on a wheelchair.

Another field of art pertinent to the present invention is that of isokinetic systems, such as those disclosed in U.S. Pat. No. 4,711,450 to McArthur, U.S. Pat. No. 4,885,939 to Martin, and U.S. Pat. No. 4,601,468 to Bond et al. These devices are generally large, non-portable, single function machines, and must be operated by trained professionals. Some of the devices in this category are able to adjust the level of resistance to movement as either more resistance or less resistance, however, their use is limited to diagnostic measurement of a single joint, and a different device is used for actual therapy sessions.

Other than emergency stop procedures, the data collection of the above referenced devices is limited to collection of data for use in subsequent therapeutic sessions. None of these devices is configured to collect data in real time for substantially immediate implementation.

There is therefore a need for a portable orthotic system that collects data regarding limb movement, (displays representations of the data in real time, and modifies current device function based upon such data so as to meet pre-defined therapeutic treatment parameters with regard to device-actuated movement needs of the limb regarding device-actuated movement, and/or assist limb rotation. It would be of benefit if the system could be operated by a patient, at least during therapy sessions and when used as an assistive device. It would be of further benefit if the system could be used outside of a clinic, such as in a patient's home, with data communication to a clinic.

SUMMARY OF THE INVENTION

The present invention is a portable orthotic system that collects data regarding limb movement, displays representations of the data in real time, and modifies current device function based upon such data so as to meet predefined therapeutic treatment parameters with regard to device-actuated movement needs of the limb regarding device-actuated movement, and/or assist limb rotation.

According to the teachings of the present invention there is provided a method for moving a jointed body part of a patient through a range of motion, the method comprising: (a) deploying an external actuating device on the patient; (b) activating the external actuating device so as to repeatedly perform a set of motions according to a certain set of parameters; (c) collecting data relating to the performance; (d) analyzing the data by use of a data processor, the analyzing being substantially in real time; and (e) (luring the activating, modifying, responsive to the data, at least one parameter of the set of parameters during an uninterrupted treatment session.

According to a further teaching of the present invention, the set of motions includes rotating the body part about a first axis of body-part-rotation According to a further teaching of the present invention, the external actuating device is implemented with at least two rotatably interconnected sections, the deployment being such that a first axis of device-rotation, which is an axis about which the sections rotate in relation to each other, lies substantially on the first axis of body-part-rotation.

According to a further teaching or the present invention, the activating includes rotating at least one of the sections about the first axis of device-rotation.

According to a further teaching of the present invention, the at least two rotatable sections are implemented as at least three sections having a first and second axes of device-rotation, which are axes about which the sections rotate in relation one to another, that lie substantially on a first and second axes of body-part-rotation.

According to a further teaching of the present invention, the rotating of the sections about the axis of device-rotation is implemented as rotation about the first and second axes of device-rotation, and the first and second axes of device-rotation are perpendicular to each other.

According to a further teaching of the present invention, the rotating about the first and second axes of device-rotation is implemented as substantially simultaneous rotation about the first and second axes of device-rotation.

According to a further teaching of the present invention, the collecting data includes collecting data regarding angular orientation of each one of the sections in relation to others of the sections.

According to a further teaching of the present invention, the collecting data includes collecting force related data.

According to a further teaching of the present invention, the collecting data includes collecting time related data.

According to a further teaching of the present invention, the parameters include angular movement velocity of at least one of the sections.

According to a further teaching of the present invention, the parameters include force applied by at least one the section to the body part.

According to a further teaching of the present invention, the parameters include time of the activating of the external actuating device.

According to a further teaching of the present invention, the activating further includes using a control unit in electronic communication with the data processor, the control unit further being in control communication with the external actuating device.

According to a further teaching of the present invention, there is also provided activating hydraulic actuators associated with the external actuating device to achieve the rotation, the control communication therefore being fluid communication.

According to a further teaching of the present invention, the control unit is implemented as a remote control unit.

According to a further teaching of the present invention, there is also provided displaying representations of the data.

According to a further teaching of the present invention, the displaying is implemented as a substantially continuous, real time display of the data.

According to a further teaching of the present invention, the certain set of parameters relate to the activating being in a rehabilitative mode.

According to a further teaching of the present invention, the certain set of parameters relate to the activating being in an assistive mode.

According to a further teaching of the present invention, the data collecting includes saving the data for later retrieval.

According to a further teaching of the present invention, the saving includes adding the data to a database.

According to a further teaching of the present invention, the database in implemented as a patient dedicated database.

According to a further teaching of the present invention, the database is implemented as a system database.

According to a further teaching of the present invention, the analysis includes analysis of data in the database.

According to a further teaching of the present invention, the analysis includes comparison of data from a current session to data from at least one previous session.

According to a further teaching of the present invention, the analysis includes comparison of data from a current session to data in the database.

According to a further teaching of the present invention, the analysis includes analysis of rehabilitative progress.

According to a further teaching of the present invention, the analysis is included in a decision making process of a treatment team.

There is also provided according to the teachings of the present invention, a system for moving a jointed body part of a patient through a range of motion, the system comprising: (a) an external actuating device deployed on the patient configured so as to repeatedly perform a set of motions according to a certain set of parameters; (b) data collection elements associated with the external actuating device configured so as to collect data relating to the rotation; (c) a data processor in data communication with the data collection elements and control communication with the external actuating device, the data processor configured so as to analyze the data in real time and during the performance of the set of motions, modify, responsive to the data, at least one parameter of the set of parameters during an uninterrupted treatment session.

According to a further teaching of the present invention, the external actuating device is configured to rotate the joint of the body part.

According to a further teaching of the present invention, the external actuating device is configured with at least two rotatably interconnected sections, the external actuating device deployed such that a first axis of device-rotation, which is an axis about which the sections rotate in relation to each other, lies substantially on a first axis of body-part-rotation, and activating the external actuating device rotates at least one of the sections about the axis of device-rotation, thereby articulating the body part.

According to a further teaching of the present invention, the at least two rotatable sections are implemented as at least three sections having a first and second axes of device-rotation, which are axes about which the sections rotate in relation one to another, that lie substantially on a first and second axes of body-part-rotation.

According to a further teaching of the present invention, the first and second axes of device-rotation are perpendicular to each other.

According to a further teaching of the present invention, the rotating about the two axes of device-rotation is implemented as substantially simultaneous rotation about the two axes of device-rotation.

According to a further teaching of the present invention, the data collecting elements include elements configured to collect data regarding angular orientation of each one of the sections in relation to others of the sections.

According to a further teaching of the present invention, the data collecting elements include elements configured to collect force related data.

According to a further teaching of the present invention, the data collecting elements include elements configured to collect time related data.

According to a further teaching of the present invention, the data collection elements include a tension/compression load cell According to a further teaching of the present invention, the data collection elements include an encoder.

According to a further teaching of the present invention, the data collection elements include a torque sensor.

According to a further teaching of the present invention, the certain set of parameters includes angular velocity of at least one of the sections.

According to a further teaching of the present invention, the certain set of parameters includes force exerted by at least one of the sections.

According to a further teaching of the present invention, the certain set of parameters includes time during which the external actuating device is activated.

According to a further teaching of the present invention, there is also provided a control unit in electronic communication with the data processor, and in control communication with the external actuating device.

According to a further teaching of the present invention, there is also provided hydraulic actuators associated with the external actuating device, the hydraulic actuators configured so as to rotate the sections about the axis of device-rotation, the control communication therefore being fluid communication.

According to a further teaching of the present invention, the data collection elements in include a fluid pressure sensor.

According to a further teaching of the present invention, the control unit is implemented as a remote control unit.

According to a further teaching of the present invention, the data processor includes a display component configured to display representations of the data.

According to a further teaching of the present invention, the data processor is configured such that the display of data representations is a substantially continuous, real time display of the data.

According to a further teaching of the present invention, the data is saved for later retrieval.

According to a further teaching of the present invention, the data is added to a database.

According to a further teaching of the present invention, the database in implemented as a patient dedicated database.

According to a further teaching of the present invention, the database is implemented as a system database.

According to a further teaching of the present invention, the data processor analyzes the data in the database.

According to a further teaching of the present invention, the data processor is configured to compare data from a current session to data from at least one previous session.

According to a further teaching of the present invention, the data processor is configured to compare data from a current session to data in the database.

According to a further teaching of the present invention, the data processor is configured to analyzes rehabilitative progress.

According to a further teaching of the present invention, the data processor is configured to provide data to aid a decision making process of a treatment team.

BRIEF DESCRIPTION OF THE DRAWINGS

The invention is herein described, by way of example only, with reference to the accompanying drawings, wherein:

FIG. 14 is a table representation of data collected during classical muscle testing according to the teachings of the present invention;

DESCRIPTION OF THE PREFERRED EMBODIMENTS

Figure 1:
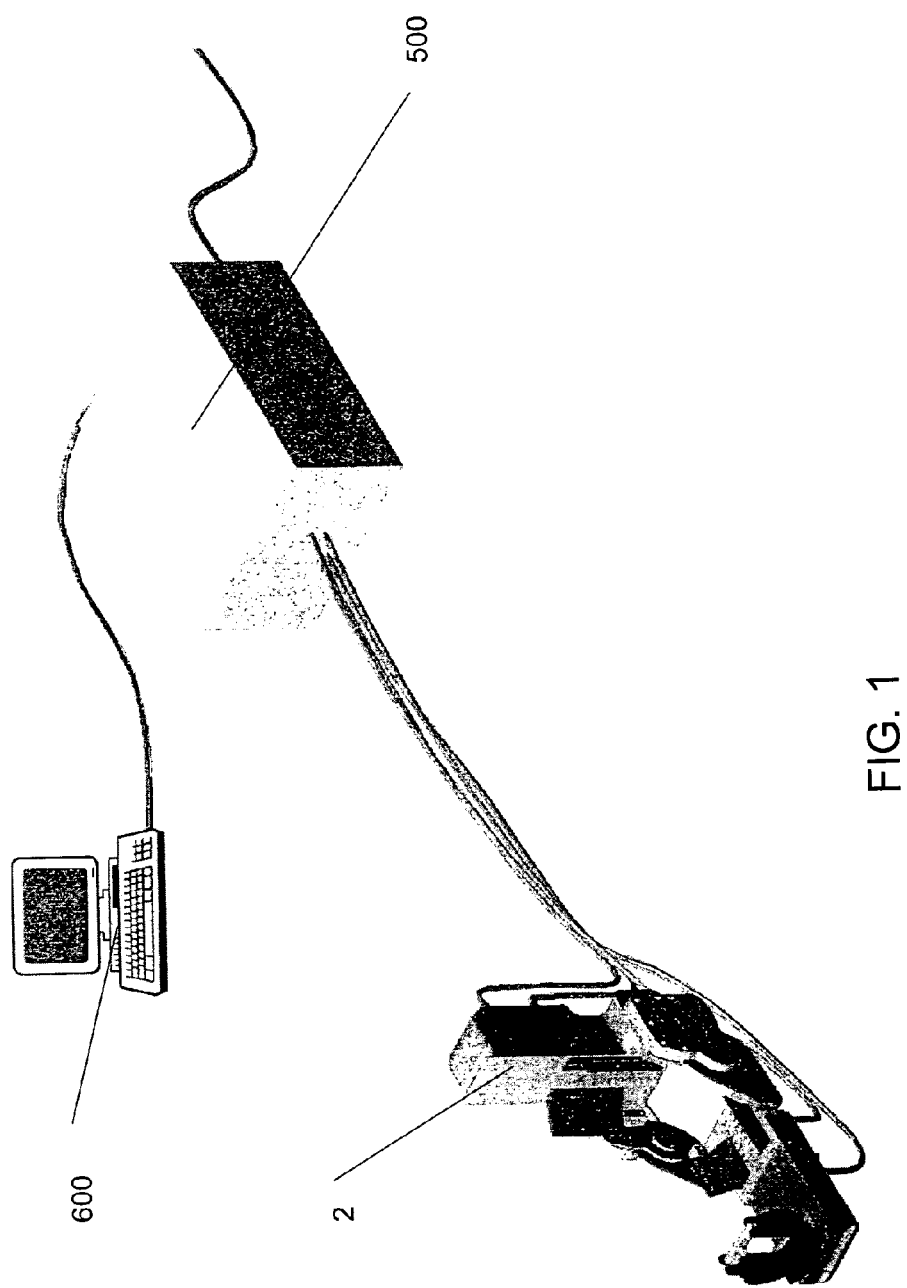
FIG. 1 is an "artist view" of an orthotic system constructed and operative according to the principles of the present invention.

The present invention is a portable orthotic system that collects data regarding limb movement, displays representations of the data in real time, and modifies current device function based upon such data so as to meet predefined therapeutic treatment parameters with regard to device-actuated movement needs of the limb regarding device-actuated movement, and/or assist limb rotation.

The principles and operation of an orthotic system according to the present invention may be better understood with reference to the drawings and the accompanying description.

By way of introduction, the non-limiting example of an orthotic system herein described relates to all orthesis for the elbow and forearm. It should be noted that the principles of the present invention may be applied to devices configured to rotate substantially any jointed body part, such as, but not limited to, the shoulder, the hip, the knee, and the spine. Further, the principles of the present invention need not be limited solely to devices for humans; therefore, veterinary devices are within the scope of the present invention.

A principle of the present invention is to collect and analyze data relating to the response of the patient to the movement of the external actuating device during a treatment session. The system then modifies at least one operational parameter of the system so as to optimize the rehabilitative process performed by the system. Prior art systems are known to change device functions so as to meet predefined operational parameters, such as constant velocity through a range of motion. The present invention by contrast, modifies the operational parameters so as to meet or maintain an optimal rehabilitative level. For example, isokinetic device of prior art will modify the amount of resistive force so as to maintain a predefined velocity. The system of the present invention will redefine the velocity parameter if the rehabilitative level falls outside of a predefined optimal range. The operational difference between the prior art systems and the system of the present invention is that each time the patient moves in the same way, the devices of prior art will make the response. The system of the present invention, however will determine if the movement of the patient falls outside of the optimal rehabilitative range, and if it does, will make a different response on successive occurrences of the movement.

Another principle of the present invention is the storage and retrieval of the patient related data from each assessment and/or treatment session. Such data may form a database, data from which may be used for long term analysis of, by non-limiting example, treatment effectiveness, rehabilitative progress monitoring, attainment of treatment benchmarks, and to aid in the decision making process of the treatment team. Data analysis may be in the form of, by non-limiting example, comparing the data sets resulting from previous sessions with the new acquired data from a current session while the session is in progress or at the termination of the session, or analysis of the full database to determine attainment of treatment or rehabilitative benchmarks. Such benchmarks may include, by non-limiting example, attainment of maximum rehabilitative level. This may be determined by attainment of predefined amount of limb use, such as full or 75% of lime use, or through data analysis showing a leveling off of rehabilitative progress, at which point, a percentage of limb use may be determined and a level of disability assigned.

Data supplied by the system may aid in the decision-making of the treatment team based on the progress monitoring, where the control program may suggest changes in the rehabilitation process based on rules defined by the physician/doctor or stored in the program is an expert knowledge database. Using these features, it will be possible to make patient-related or hospital-related decisions, such as, but not limited to, ending hospitalization or treatment, changes in the treatment regimen, assigning a certain disability level to the patient, changing the function of the orthotic system from a rehabilitative device to an assistive device.

The following description will first discuss a preferred embodiment of an orthotic system constructed and operative according to the principles of the present invention configured for rotation of the elbow and forearm (FIGS. 1–9), and then discuss the operation of the device in two different modes of operation, rehabilitative mode (FIGS. 10–22) and assistive mode.

The preferred embodiment of an orthotic system according to the teachings of the present invention illustrated in FIG. 1 includes an external actuating device 2, and remote control unit 500 and an external computer 600.

Figure 2:
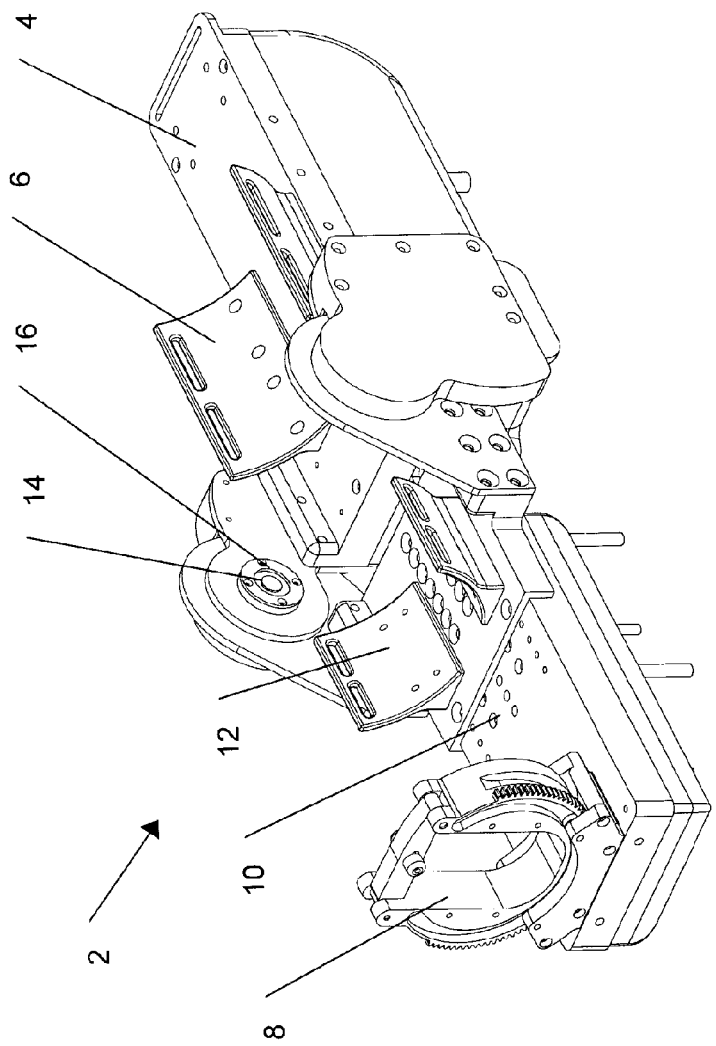
FIG. 2 is a perspective view of an external actuating device constructed and operative according to the principles of the present invention.

FIG. 2 illustrates a preferred embodiment of an external actuating device 2 constructed and operative according to the principles of the present invention. The upper arm section 4 of the external actuating device 2 is held on the upper arm of the patient by use of preferably Velcro®, straps (not shown) used in association with the tipper arm attachment element 6. The forearm, near the wrist, of the patient is placed into the forearm rotator 8, and the forearm section 10 of the external actuating device 2 is held in place by use of, preferably Velcro®, straps (not shown) associated with the forearm attachment element 12. The place of the external actuating device 2 of the arm of the patient is such that a first axis of rotation 14 of the rotatable interconnecting hinge 16, connecting the upper arm section 4 to the forearm section 10, lies substantially on the axis of rotation of the patient's elbow joint. The first axis of rotation will be referred to here in the description as the "elbow axis of rotation." In such a deployment, activating rotation of the external actuating device about the elbow axis of rotation rotates the patients elbow joint.

Figure 3A:
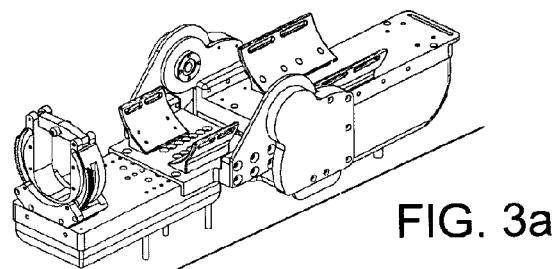
FIGS. 3a–3d are a series of perspective views of the embodiment of FIG. 2, showing rotation of an external actuating device though a range of rotation from 0° to 135°.
Figure 3B:
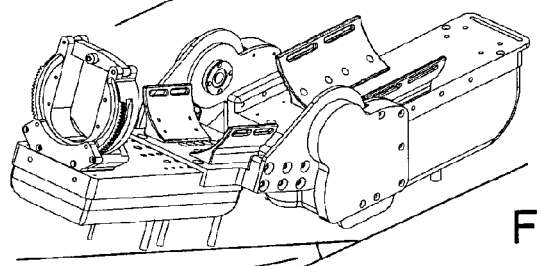
Figure 3C:
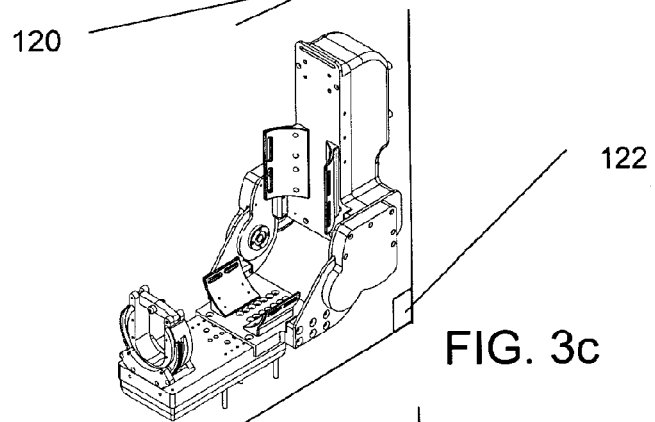
Figure 3D:
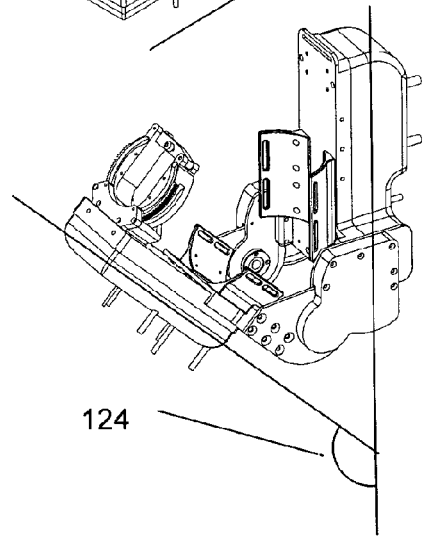

FIGS. 3a–3d illustrate rotation of the external actuating device about the elbow axis of rotation. FIG. 3a illustrates 0° of rotation; FIG. 3b illustrates 20° of rotation 120; FIG. 3c illustrates 90° of rotation 122; and FIG. 3d illustrates 135° of rotation 124.

Axial rotation of the patient's forearm is accomplished by rotation of the forearm rotator 8, which is configured so as to rotate 180° about a second axis of rotation that runs substantially longitudinally through the center of the forearm and substantially perpendicular to the elbow axis of rotation. The second axis of rotation will be referred to here in the description as the "forearm axis of rotation."

Figure 4:
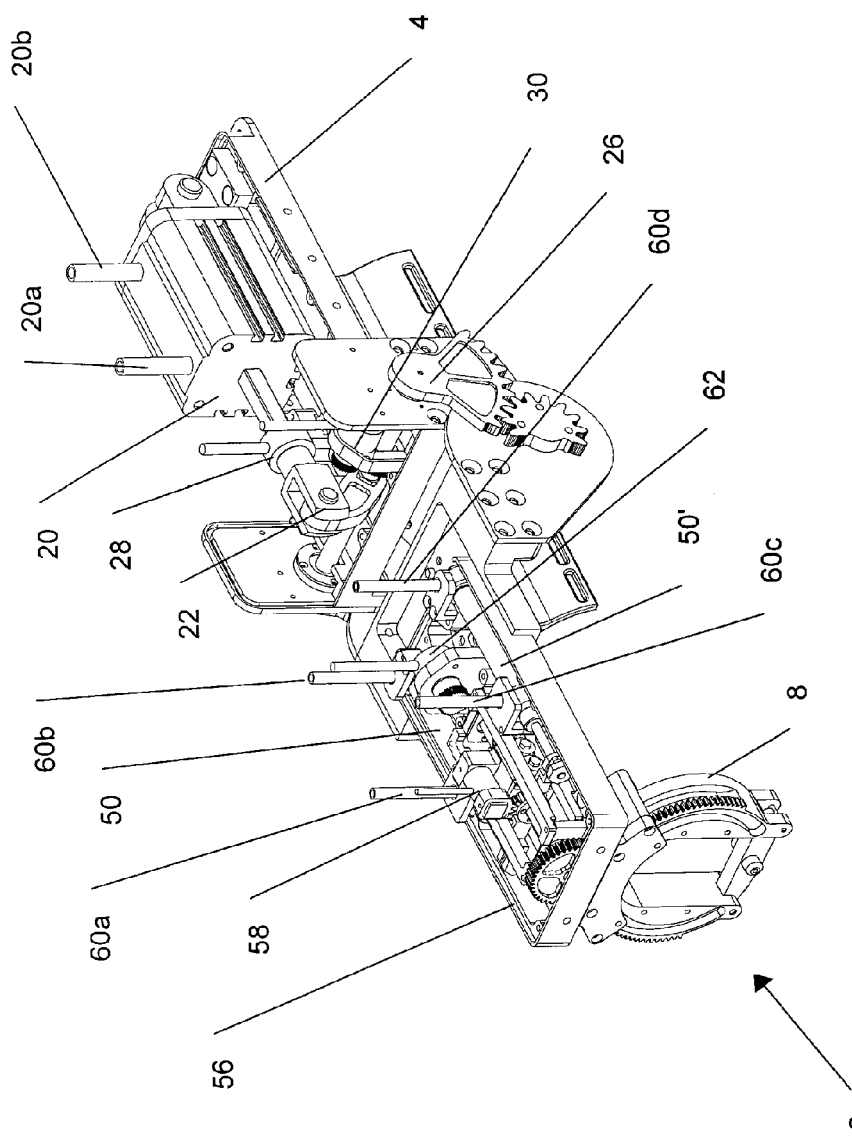
FIG. 4 is a perspective view of the bottom side of the embodiment of FIG. 2 shown with housing covers removed so as to expose internal operative elements of the device.
Figure 5:
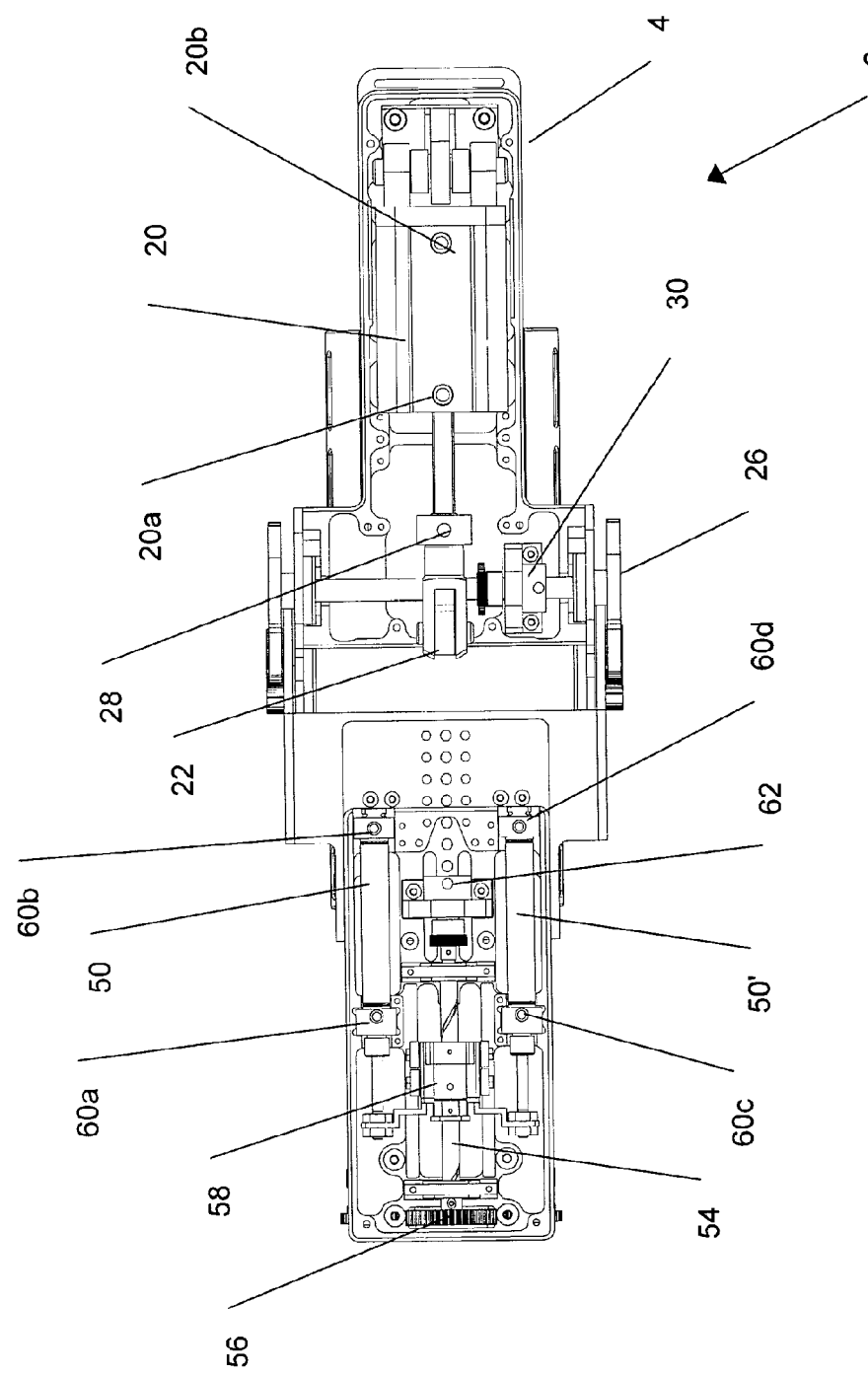
FIG. 5 is a top elevation of the embodiment of FIG. 2.
Figure 6:
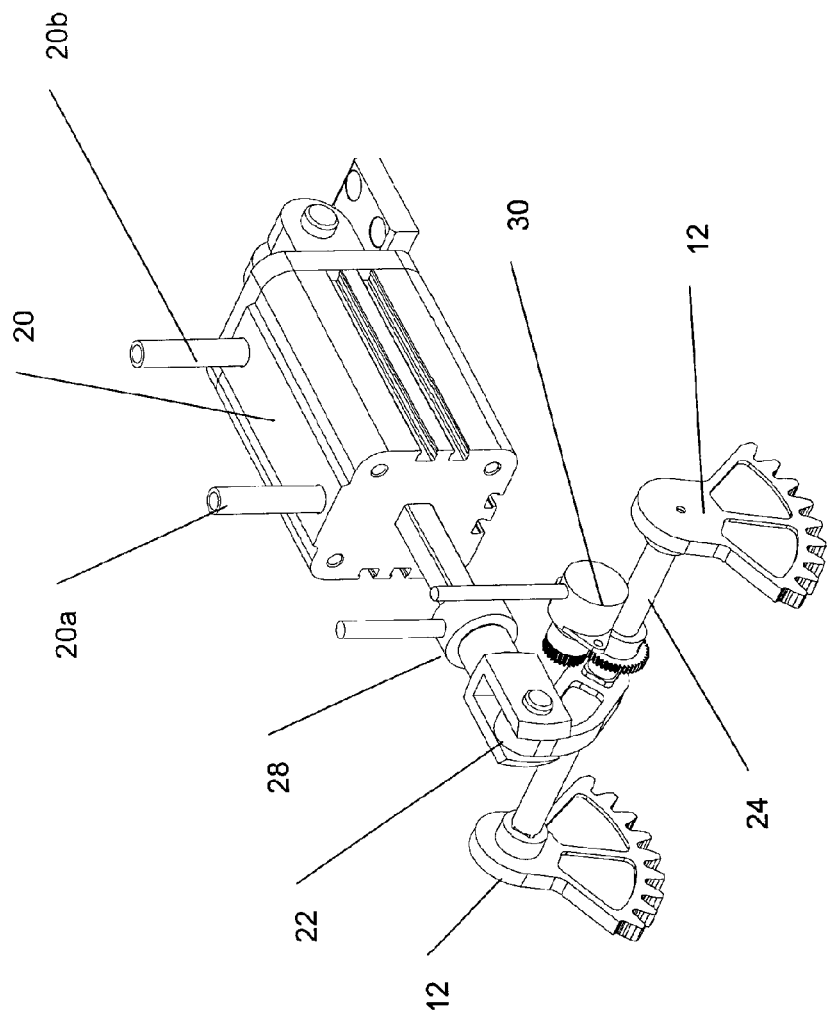
FIG. 6 is a perspective view of operational elements deployed in the upper arm section of the embodiment of FIG. 2.
Figure 7:
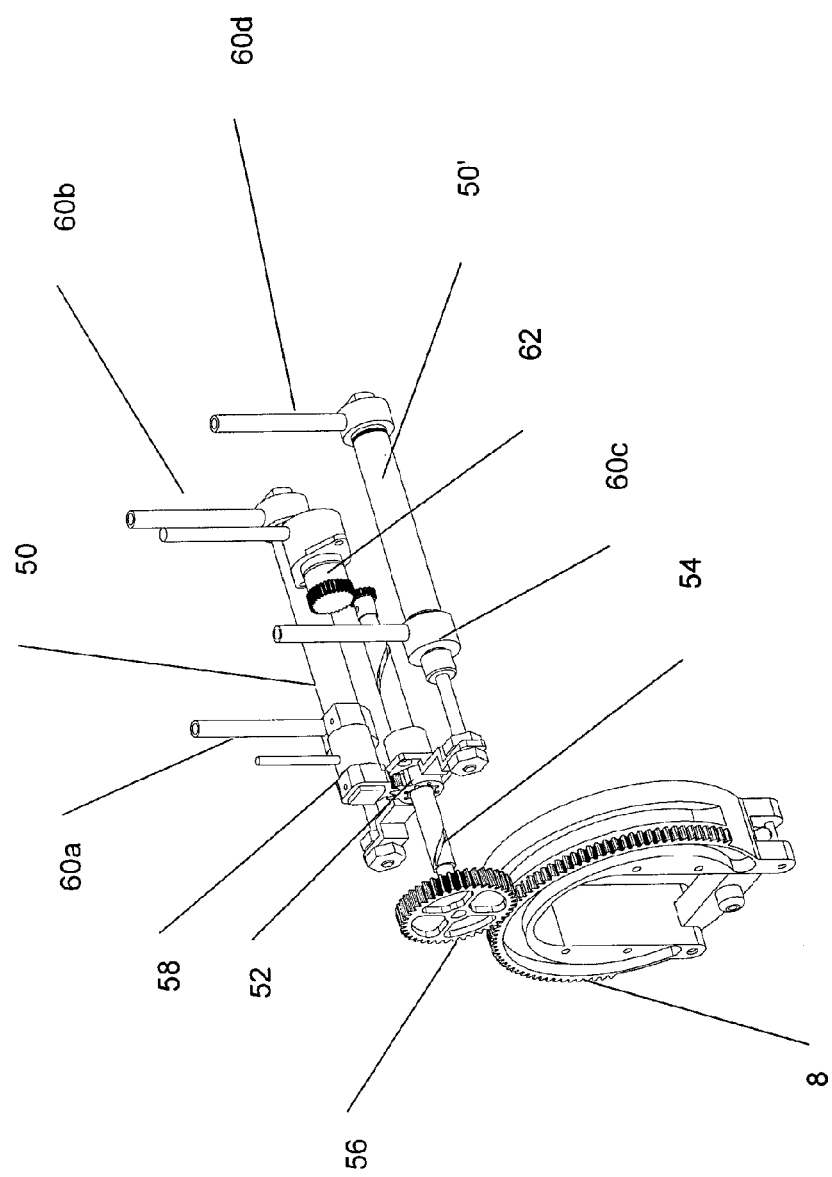
FIG. 7 is a perspective view of operational elements deployed in the forearm section of the embodiment of FIG. 2.

FIG. 4 (perspective) and 5 (top elevation) provide similar views of mechanical elements of the external actuating device with out housing covers, and are therefore similarly numbered. The elbow rotation mechanism, located in the upper arm section 4, provides rotation about the elbow axis of rotation whereby linear movement of piston 20 in association with lever 22 causes the rotation of axle 24 and thereby rotation of gears 26 (see also detail FIG. 6). Piston 20 is preferably a bi-directional hydraulic piston in fluid communication with a control injector piston located in the remote control unit 500 though hydraulic lines 20a and 20b. Data collection elements such as but not limited to, a tension/compression load cell 28 and encoder 30 may also be associated with the elbow rotation mechanism, and be in data communication with the data processor in the control unit or with the external computer, to provide real time data for, by non-limiting example, real time device operational modifications, and treatment evaluation and assessment.

Figure 8:
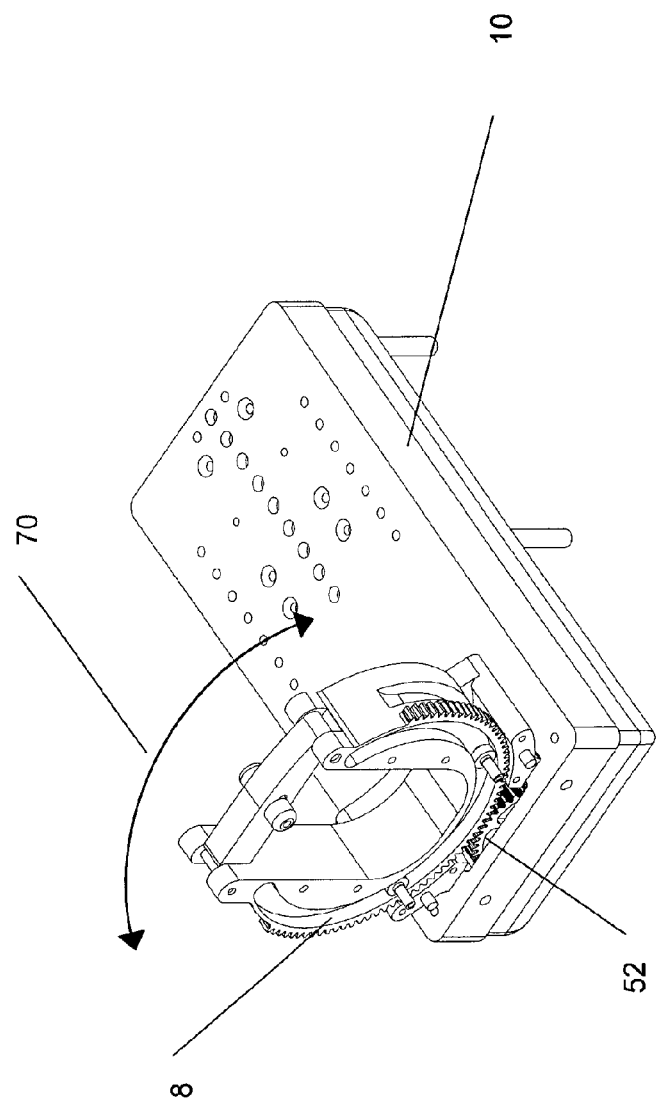
FIG. 8 is a perspective view of a forearm section of the embodiment of FIG. 2.

The forearm rotation mechanism, located in the forearm section 10, provides rotation about the forearm axis of rotation whereby linear movement of pistons 50 and 50' in association with linear slide bolt 52 causes the rotation of helical rod 54 and thereby rotation of gear 56, which in turn rotates the forearm rotator 8 (see also detail FIGS. 7 and 8) throughout a range of substantially 180°, as indicated by arrow 70 in FIG. 8. Pistons 50 and 50' are preferably bi-directional hydraulic pistons in fluid communication with a control injector piston located in the remote control unit 500 though hydraulic lines 60a–60d. Data collection elements such as but not limited to, a load cell 58 and encoder 62 may also be associated with the elbow rotation mechanism, and be in data communication with the microprocessor, to provide real time data for, by non-limiting example, real time device operational modifications, and treatment evaluation and assessment.

Figure 9:
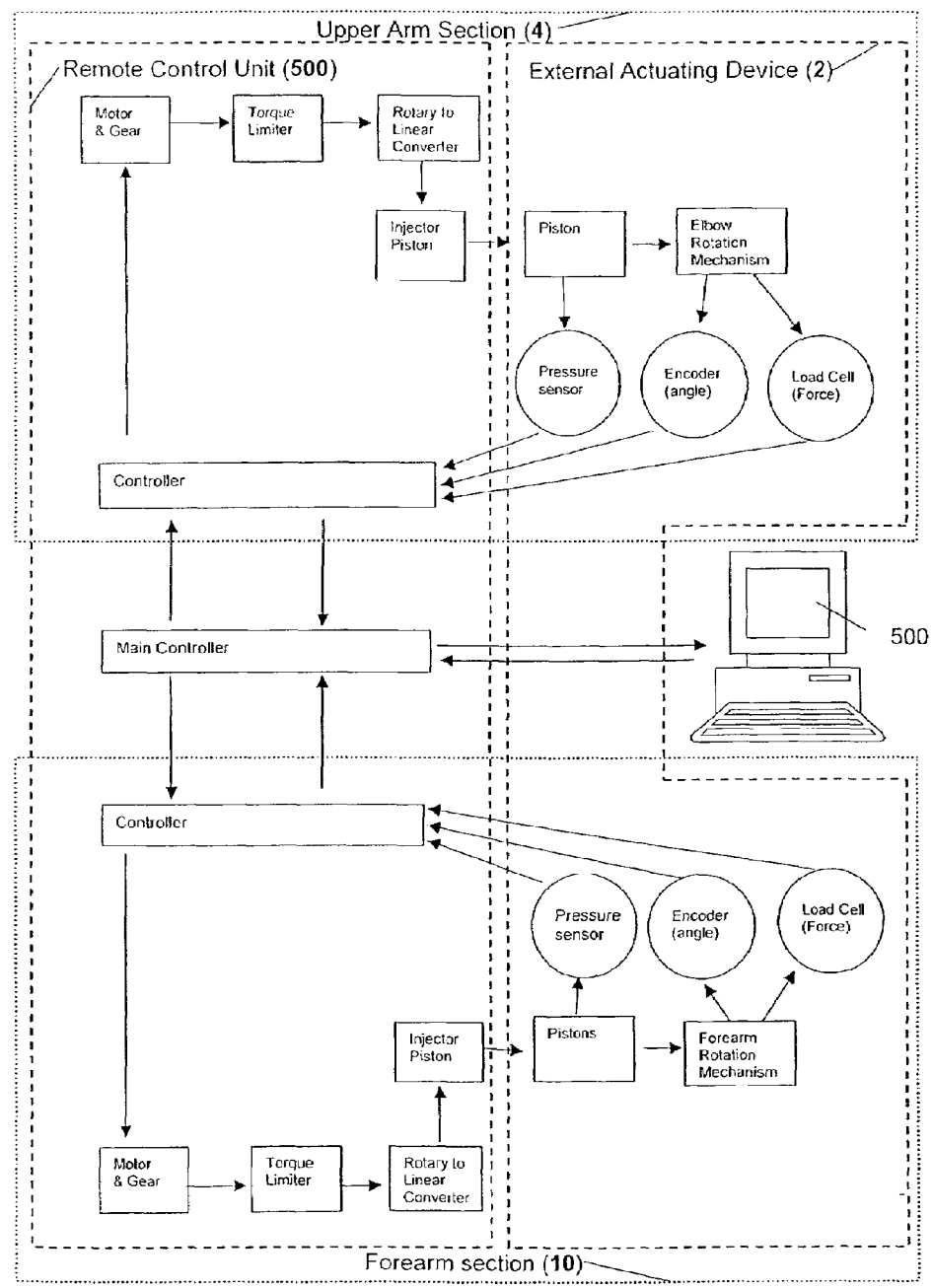
FIG. 9 is a block diagram showing the physical location and operational association of operational elements of the system of FIG. 1.
Figure 10:
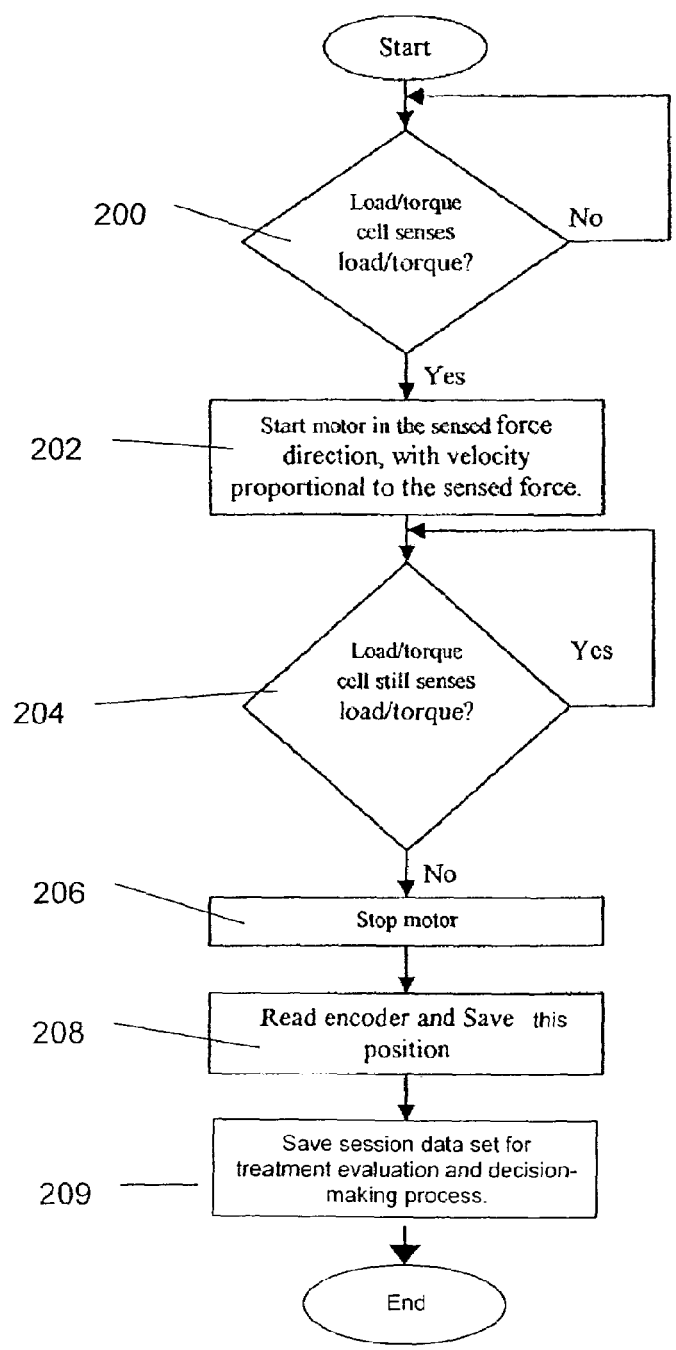
FIG. 10 is a flow chart of an assessment of active range of motion according to the teachings of the present invention.

The block diagram of FIG. 9 illustrates the association of main operational elements of the present invention and their physical location within this embodiment of the present invention. Therefore, associated with the upper arm section 4 is a controller, a torque limiter, a rotary to linear converter, an injector piston, a piston, an elbow rotation mechanism, a pressure sensor, an encoder to measure angle of deployment, and a load cell. The controller, torque limiter, rotary to linear converter, and injector piston are physically located in the remote control unit 500. Likewise, the piston 20, elbow rotation mechanism (including lever 22, axle 24 and gears 26), pressure sensor, encoder 30, and load cell 28 are physically located in the upper arm section 4 of the external actuating device 2. Similarly, associated with the forearm section 10 is a controller, a torque limiter, a rotary to linear converter, an injector piston, a pistons, a forearm rotation mechanism, a pressure sensor, an encoder, and a load cell. The controller, torque limiter, rotary to linear converter, and injector piston are physically located in the remote control unit 500 and the pistons 50 and 50', forearm rotation mechanism (linear slide bolt 52, helical rod 54, gear 56, and forearm rotator 8), pressure sensor, encoder 62, and load cell 58 are physically located in the forearm section 10 of the external actuating device 2.

Data from the individual data collection elements is sent to the microprocessor in real time such that the current and/or on going functions of the external actuating device may be modified, responsive to the data, by modifying at least one operational parameter of a set of operational parameters during an uninterrupted treatment session.

It should be noted that while the preferred embodiment herein described relates to hydraulic actuators, however, the use of any suitable actuators known in the art is within the scope of the present invention.

Turning now to the use of an orthotic system of the present invention employed in a rehabilitative mode, the present invention provides for range of motion assessment, classical muscle testing and a treatment regimen. Here, for the ease of discussion, the description will relate, by non-limiting example, to the elbow and forearm of a patient.

To assess a patient's active range of motion, the patient is asked to move his arm so as to rotate his elbow joint. Sensors deployed on the external actuating device detect the amount and direction of the force. The data is analyzed and the external actuating device is advanced correspondingly as long as force is detected. This procedure, as illustrated in the non-limiting flowchart example of FIG. 10 for the patient's elbow joist movement, is repeated also for assessing the patient's forearm axial range of motion. As shown, when force is sensed by any one individual or combination of, load/torque cells 200 the external actuating device is advanced in the corresponding direction with proportional velocity 202. That is, the velocity may be slightly less than would have been normally achieved by the amount of force sensed so that force against the sensor will still be detected. Advancement of the external actuating device continues as long as force is sensed 204. As seen here, the force data is analyzed in real time and the corresponding operational function of the external actuating device are modified in real time so as to meet the predefined therapeutic parameter of advancing the external actuating device at a rate that will continue to detect any force exerted by the patient. That is to say, the velocity of the external actuating device is varied based on the data received from the load/torque cells. When force is no longer detected by the load/torque cells, advancement of the external actuating device is stopped 206 and the relative position of the sections in recorded 208 and the data is stored 209 and added to the patient's database.

Figure 11:
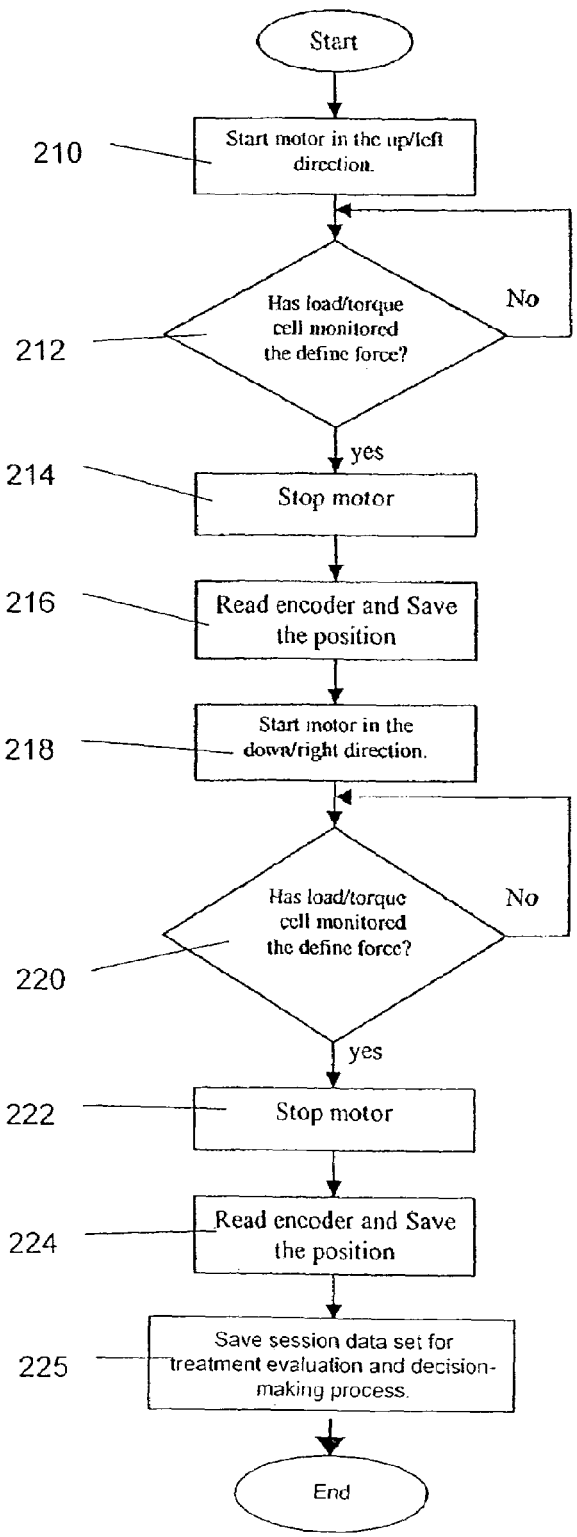
FIG. 11 is a flow chart of an assessment of passive range of motion according to the teachings of the present invention.

Assessment of passive range of motion, as illustrated in the non-limiting flowchart example of FIG. 11, entails the steps of deploying the external actuating device on the patient in a benign angular deployment, advancing the external actuating device in one direction 210, such as up or left for example, until a predefined level of resistance force is detected 212, stopping advancement 214, the relative position of the sections is recorded as a boundary of the passive range of motion 216. The process for determining the corresponding boundary entails the steps of reversing direction of the external actuating device 218, passing through the beginning angle and advancing until a predefined level of resistance force is detected 220, stopping advancement 222, the relative position of the sections is recorded as a boundary of the passive range of motion 224. All of the data from the session is saved 225, and may be added to the patient's treatment/assessment database.

Figure 12:
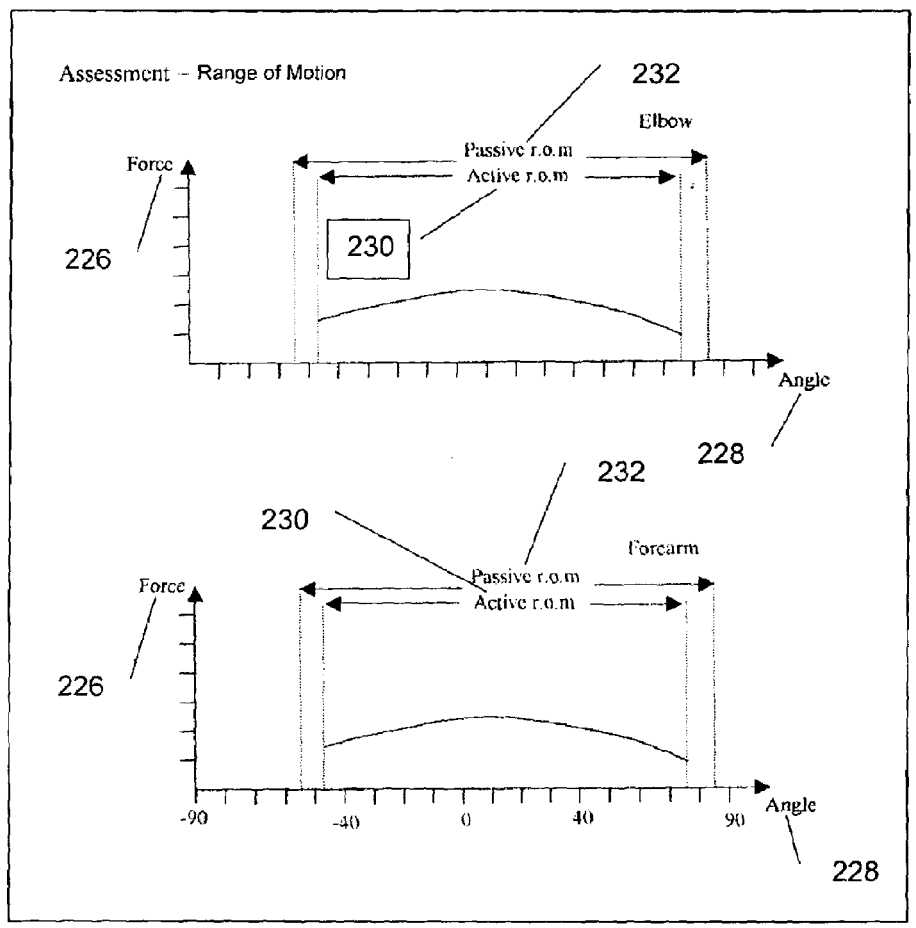
FIG. 12 is a graphic representation of data colleted during an assessment of active range of motion and/or passive range of motion according to the teachings of the present invention.

Data collected regarding the patient's ranges of motion may be displayed as a graph such as the non-limiting examples of FIG. 12, where force 226 is plotted as a function of the angle 228. It should be noted that the full ranges of both the passive 230 and active 232 ranges of motion are shown in the graphs of FIG. 12, however, according to the present invention each of the parameters may be displayed individually. Further, the data may be displayed in real time during the testing session. That is to say, it is possible to watch the graph being constructed substantially as the data is supplied to the microprocessor, as the assessment procedure is in progress. Substantially any data that may be represented in graph form may be displayed in real time.

Figure 13:
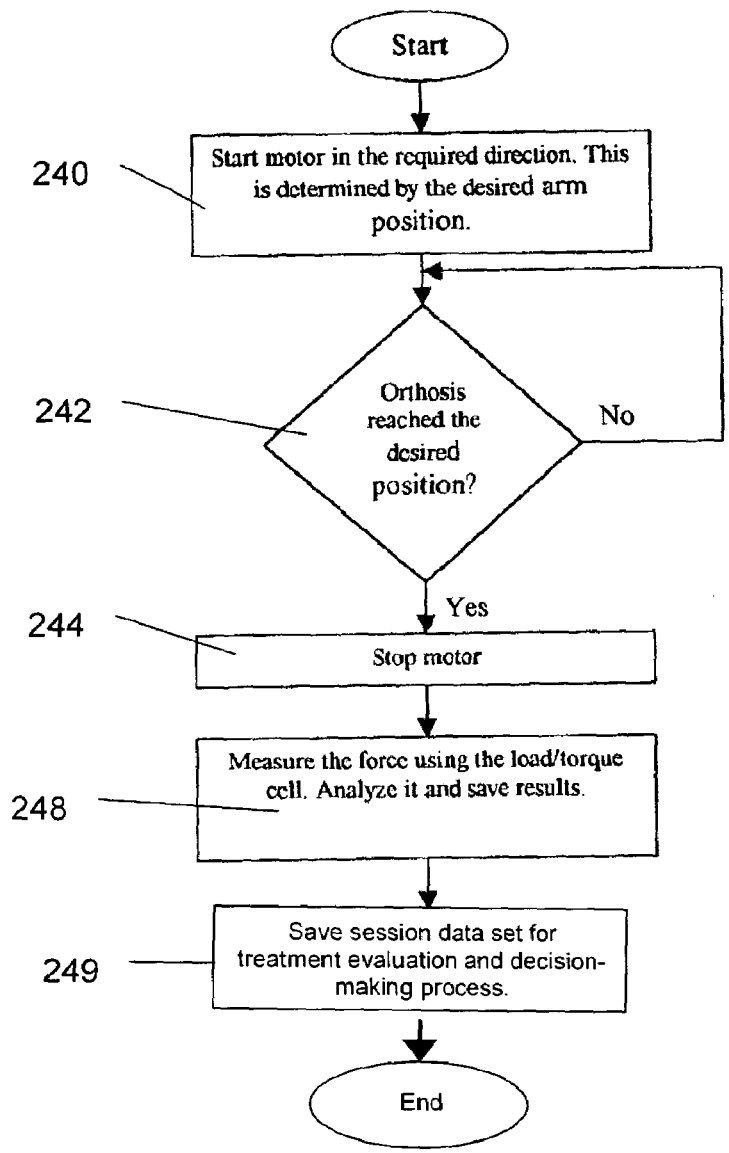
FIG. 13 is a flow chart of classical muscle testing according to the teachings of the present invention.

Classic muscle testing, as illustrated in the non-limiting flowchart example of FIG. 13, entails bringing the external actuating device to a series of predefined angular deployments (steps 240, 242 and 244) and measuring the force the patient is able to apply to the device 248. Data collected during classical muscle testing may be displayed in chart form, such as the non-limiting example illustrated in FIG. 14, which provides testing in three different positions 250 each for both the elbow 252 and the forearm 254, and records the actual force applied 256 and the force rating on a force scale of 0–5 258. All of the data from the session is saved 249, and may be added to the patient's treatment/assessment database.

A treatment regimen, as determined by a doctor or therapist, may include any one of or a combination of strain/ counter strain, isometric concentric, isotonic concentric, hold and relax, and PNF (Proprioceptive Neuromuscular Facilitation) exercises.

Figure 15:
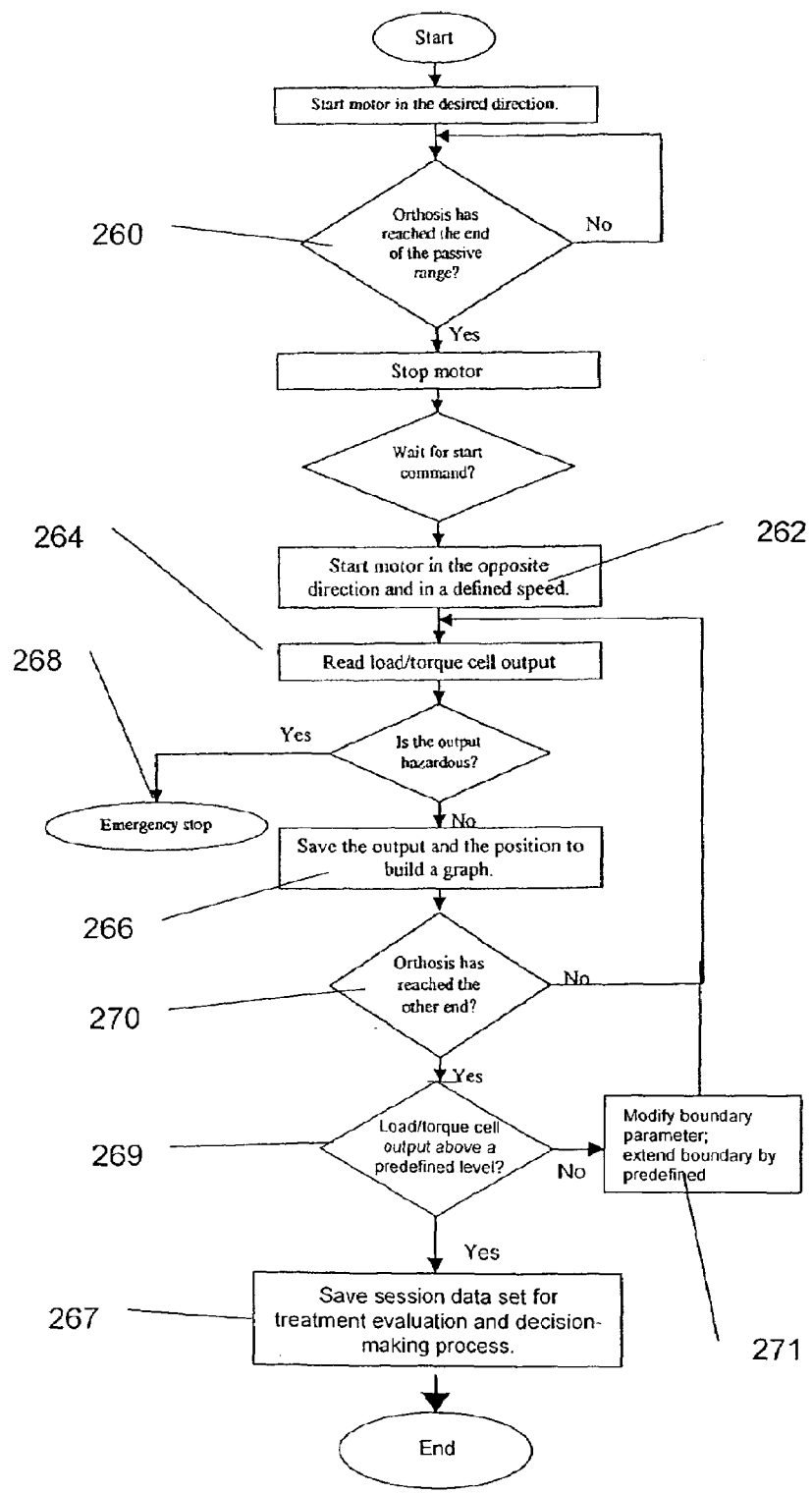
FIG. 15 is a flow chart of a strain/counter-strain treatment regimen according to the teachings of the present invention.

As the non-limiting flowchart example of FIG. 15 illustrates, operation of the orthotic system in a strain/counter-strain exercise mode according to the teachings of the present invention. The external actuating device is brought to one boundary of the patient's passive range of motion 260, and then moved in one direction through the full passive range of motion 262–270. In this manner, four different muscle groups, forearm flexors, extensors, supinators and pronators, may be isolated during treatment and worked separately, either during different treatment sessions or at different times during a single session. Data from the load and/or torque cells is monitored at a substantially constant rate 264 and the data is analyzed for display in a graphic representation 266. If a predefined emergency level of resistance in encountered, advancement of the external actuating device is stopped 268. As part of the full exercise, or as an optional Subroutine, when the opposite boundary is reached, if the patient's resistance to movement is below a predefined level 269, the boundary parameter is modified 271. Modification may be, by non-limiting example, extension of the boundary by a predefined increment or until a predefined level of resistance is met. If during the extension of the boundary, an emergency level of resistance is encountered, the new boundary may be sent at a point before the emergency level of resistance was encountered. All of the data from the session is saved 267, and may be added to the patient's treatment/assessment database.

Figure 16:
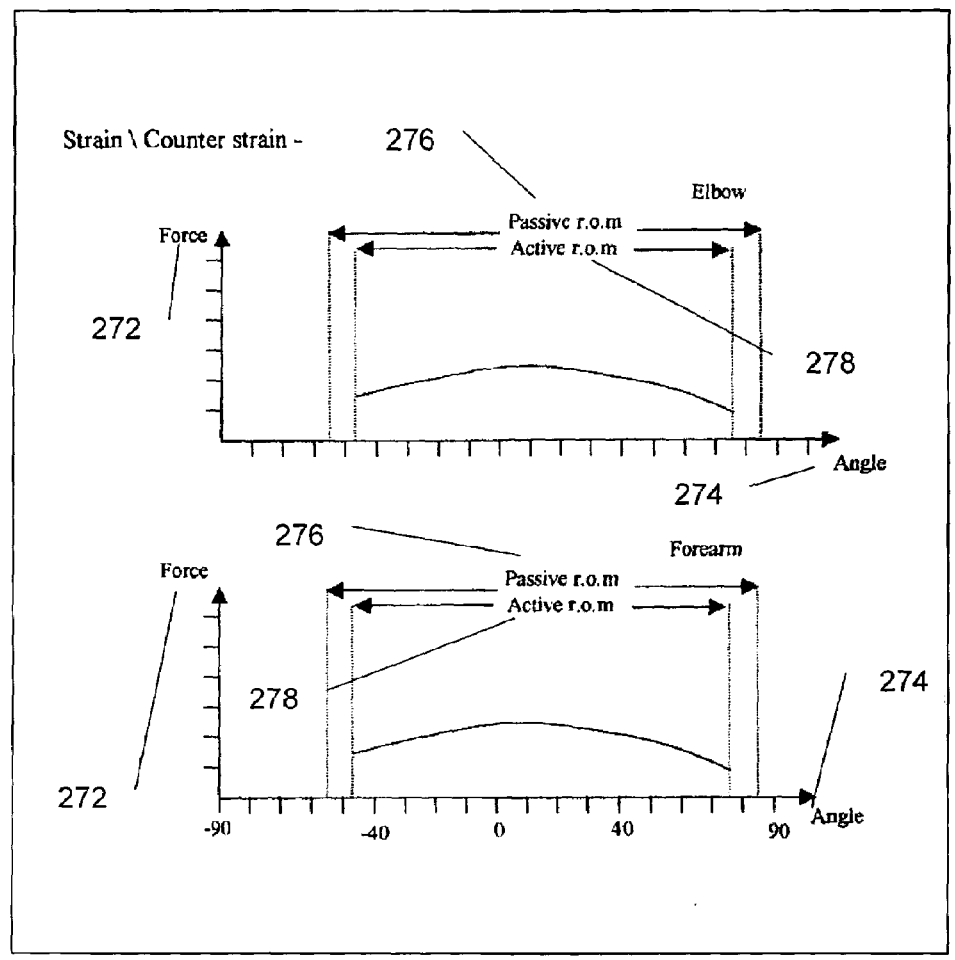
FIG. 16 is a graphic representation of data collect during a strain/counter-strain treatment session according to the teachings of the present invention.

Non-limiting examples of graphs displaying data collected during strain/counter-strain exercises are shown in FIG. 16, where force 272 is shown as a function of angle 274. Graphs for movement through the passive 276 and active 278 ranges of motion may be displayed individually or concurrently. Alternatively, data from the current session may be display concurrently with data from previous treatment or assessment sessions, data in the patient's database or the system's expert knowledge database. It should be noted that the ability to concurrently display data from any single previous treatment or assessment session, ally derivative of data in the patient's personal database, or the system's expert knowledge database is true for all of the graphs, table and charts herein discussed and is considered a principle of the present invention.

Figure 17:
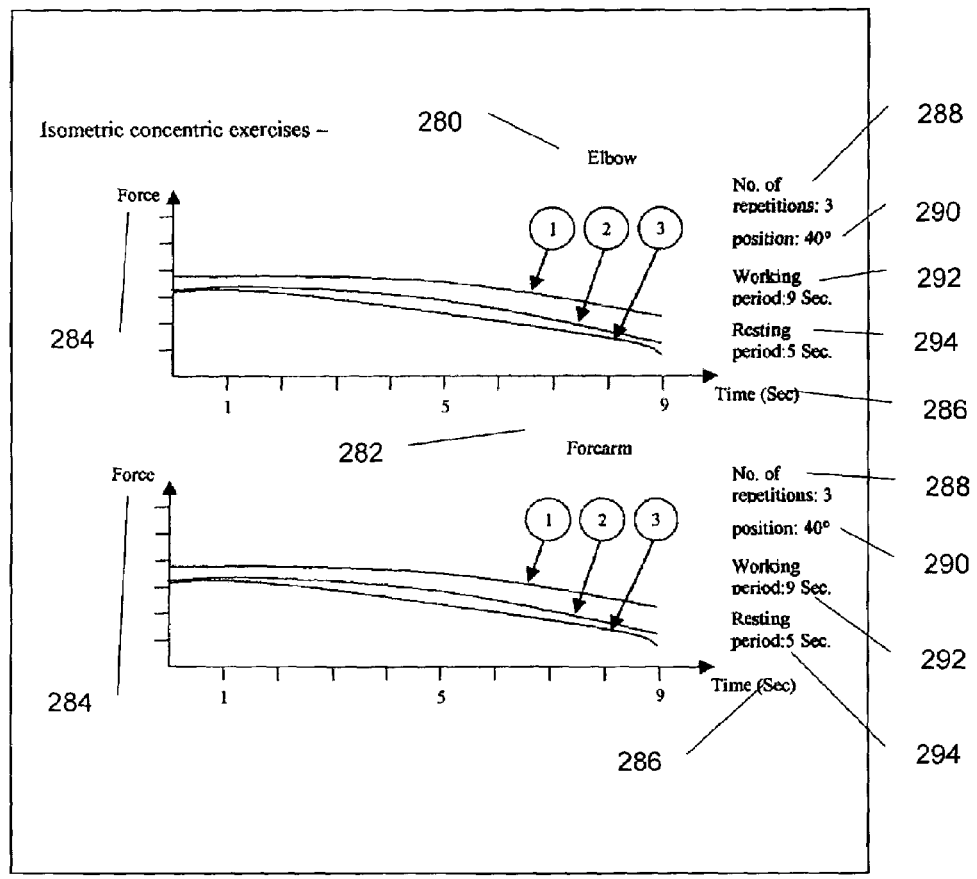
FIG. 17 is a graphic representation of data collect during an isometric concentric exercise treatment session according to the teachings of the present invention.

The procedure described above in regard to FIG. 13 for classical muscle testing may be repeated in the treatment regimen as an isometric concentric exercise. When the procedure is used as a treatment, the data displayed, as illustrated in FIG. 17 may include information relating to the elbow 280 and the forearm 282 individually in the same display. Each graph shows force 284 as a function of time 286. Other information that may be displayed may include, by non-limiting example, the number of repetitions 288, the angle of deployment at which the exercise was clone 290, the duration of the exercise 292 and the rest period between repetitions 294.

Figure 18:
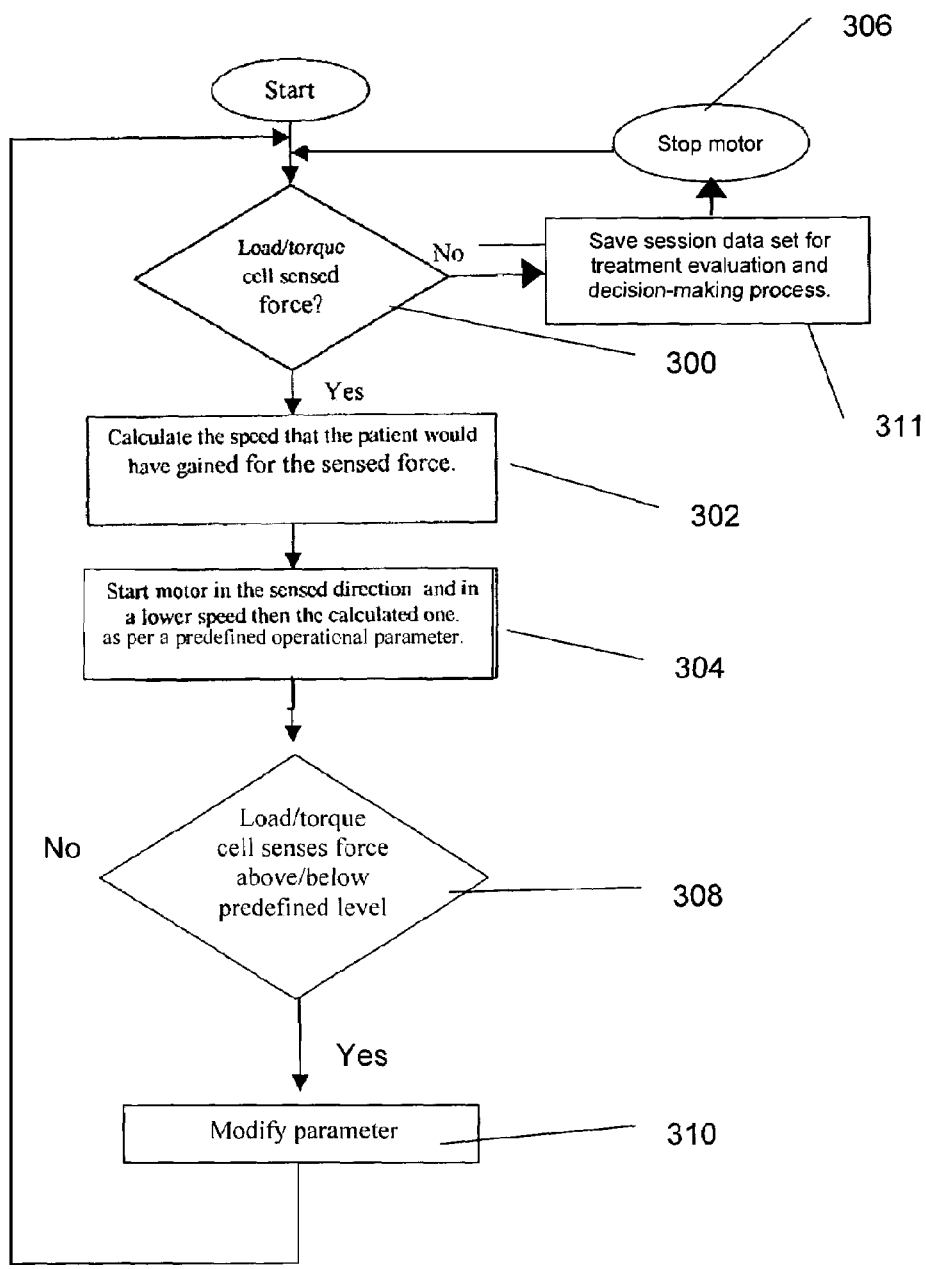
FIG. 18 is a flowchart of an isotonic concentric exercise treatment session according to the teachings of the present invention.
Figure 19:
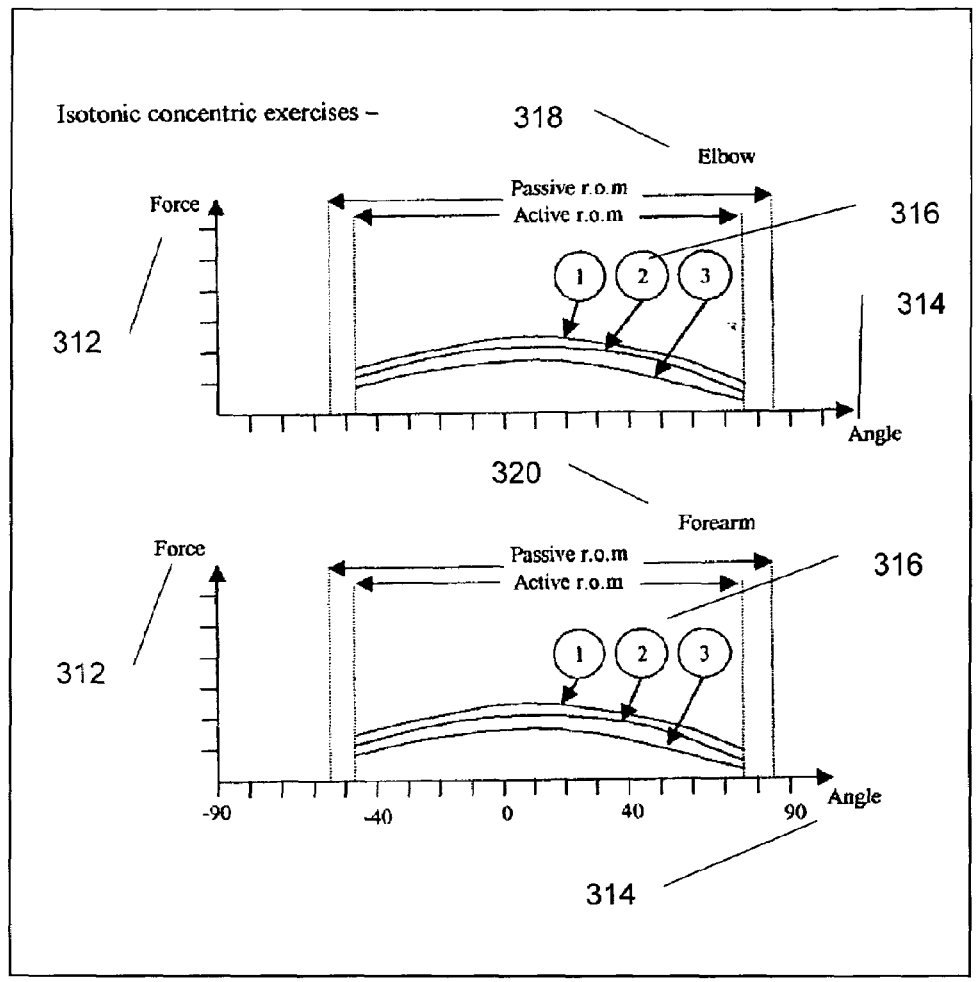
FIG. 19 is a graphic representation of data collect during an isotonic concentric exercise treatment session according to the teachings of the present invention.

The flowchart of FIG. 18 shows a non-limiting example of an Isotonic exercise according to the teachings of the present invention. The patient is told to move his arm so as to, by non-limiting example, rotate his elbow joint. Tile force of the patient is sensed by the load cell and/or torque cell 300. The velocity normally achieved by such force is calculated 302 and the external actuating device is advanced at a rate lower than that calculated 304, as per a predefined parameter so as to provide resistance to the patient. If the force sensed is above or below a predefined level 308, then the predefined parameter of step 304 is modified is step 310. The motions outlined in the above steps are followed until no force is detected, and then the advancement of the external actuating device is stopped 306. All of the data from the session is saved 311, and may be added to the patient's treatment/assessment database. It will be readily appreciated that the numerous operational parameters may be monitored and varied during an individual treatment session. A non-limiting example of a treatment regimen may be maintaining the predefined constant proportional resistance. That is, predefining that the external actuating device maintains constant rate of resistance of, by non-limiting example, 80% of patient applied force. If, however, the force applied by the patient rises above or falls below a predefined optimal rehabilitative level the proportion of resistance is modified accordingly. That is to say, if the patient applied force falls below a predefined optimal rehabilitative level the rate of resistance is modified to, for example 75% of the patient applied force. Conversely, if the patient applied force rises above a predefined optimal rehabilitative level the rate of resistance is modified to, for example 90% of the patient applied force. Therefore, according to the teaching of the present invention, if during course of a treatment session the patient applied force rises above or falls below a predefined optimal rehabilitative level, the parameter of proportion of resistance is modified without interrupting the ongoing treatment session. As illustrated in FIG. 19, the data displayed for isotonic concentric exercises may be displayed as a graphic depiction of the force 312 exerted by the patient as a function of the angle 314, and the number of repetitions 316. Graphs for each repetition may be displayed concurrently, and separate graphs may be displayed for the elbow 318 and the forearm 320.

Figure 20:
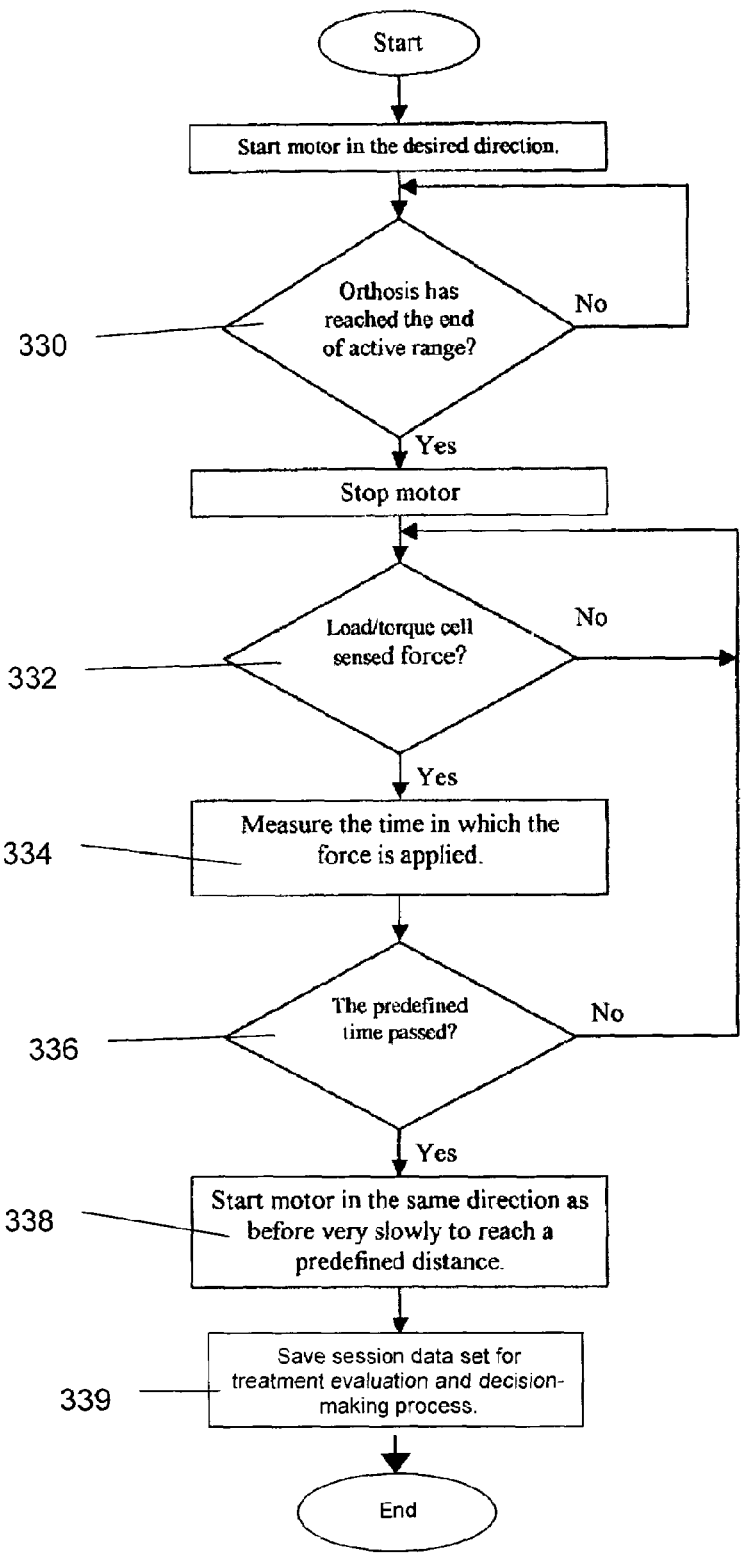
FIG. 20 is a flow chart of a relax and hold technique treatment regimen according to the teachings of the present invention.
Figure 21:
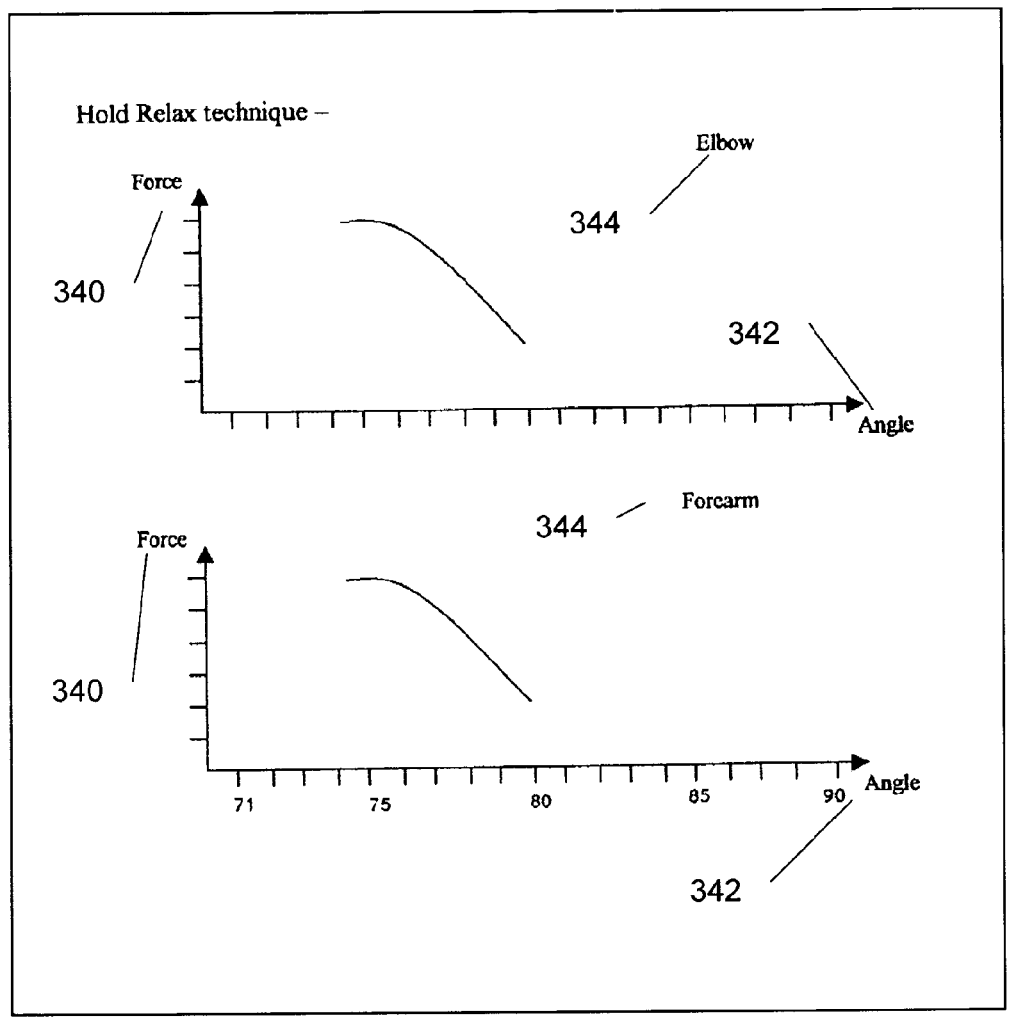
FIG. 21 is a graphic representation of data collect during a relax and hold technique exercise treatment session according to the teachings of the present invention.
Figure 22:
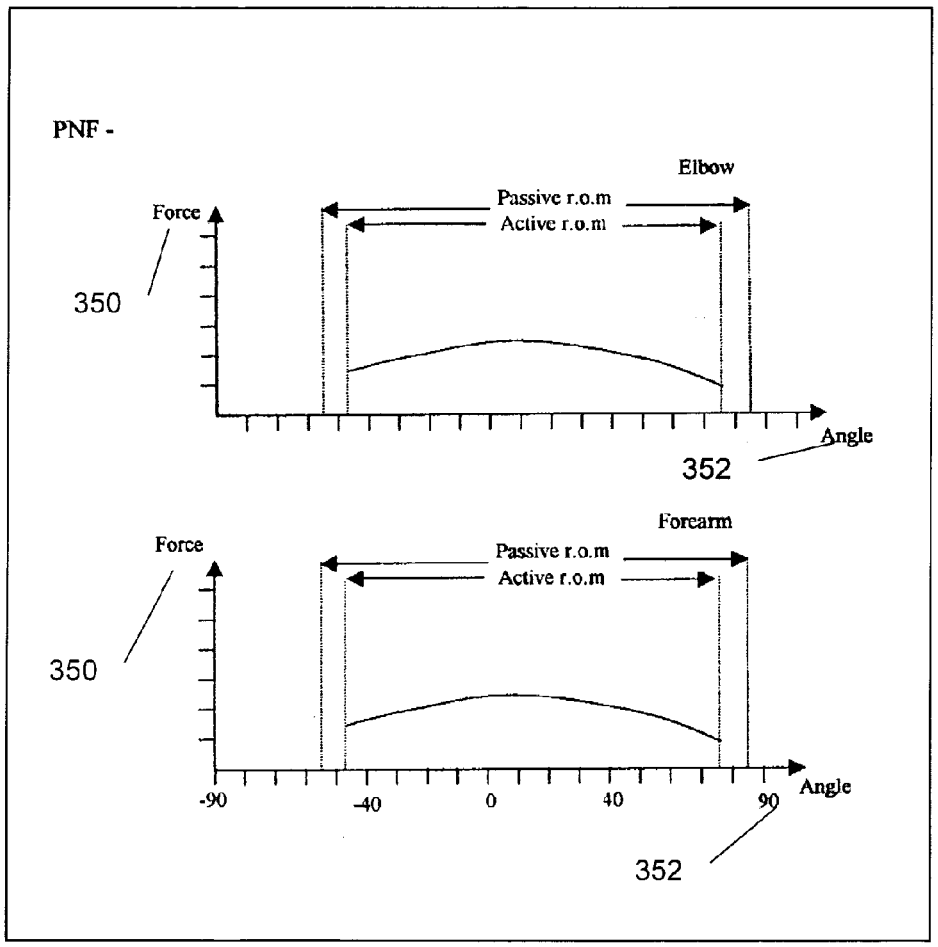
FIG. 22 is a graphic representation of data collect during a PNF exercise treatment session according to the teachings of the present invention.
Figure 23:
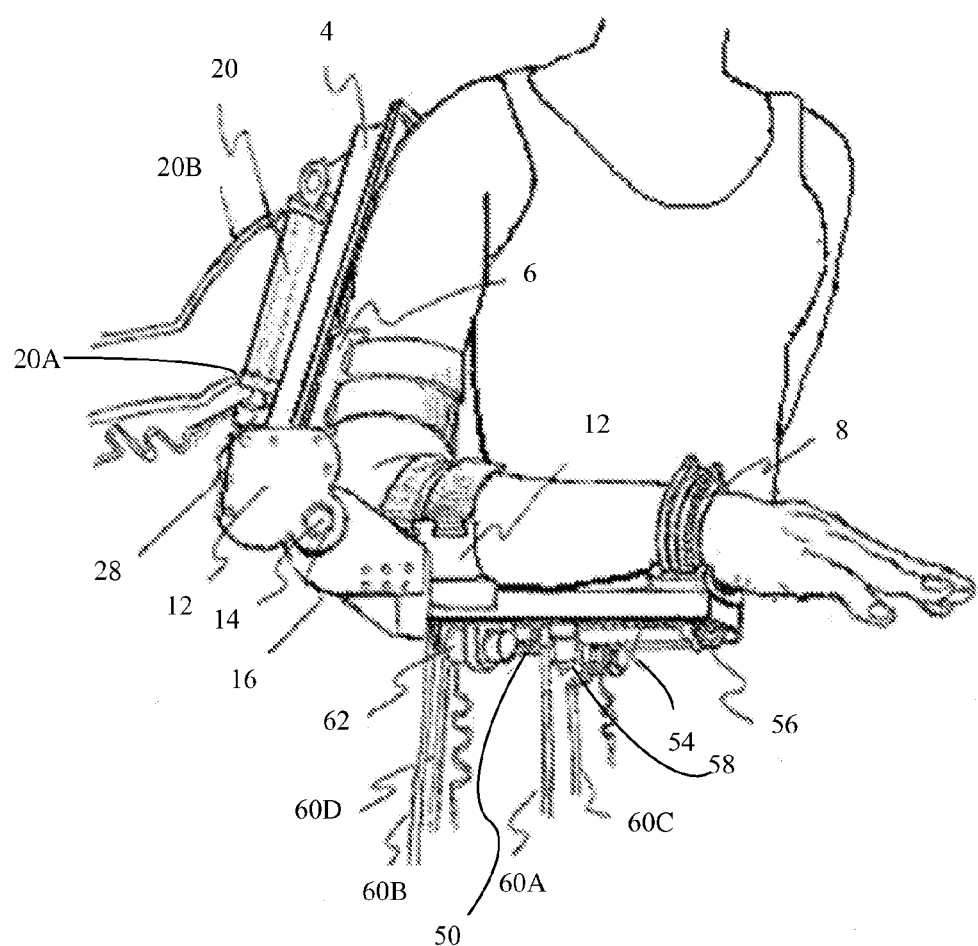
FIG. 23 is a perspective view, showing all the elements of the herein invention.

The hold and relax exercise may be used to increase either the active or passive range of motion or both. FIG. 20, is a non-limiting example of a flowchart of a hold and relax exercise to extend the active range of motion according to the teaching of the present invention. The hold and relax exercise consists of bringing the external actuating device to a predefined border of a range of motion 330, then applying force and or movement beyond the border for short predefined periods of time for a specified number of repetitions. When working in the active range, the force in supplied by the patient. In the passive range, the force is supplied by the external actuating device. The external actuating device is advanced to a boundary of the active range of motion and advancement is stopped 330. The patient is instructed to move the arm so as to rotate the, for example, elbow joint beyond the boundary and the amount 332 of and length of time 334 force is applied is monitored. After a predefined length of time 336, the external actuating device is slowly advanced beyond the range of motion boundary for a predefined distance 338, for example 5°. All of the data from the session is saved 339, and may be added to the patient's treatment/assessment database Non-limiting examples of data that may be displayed for a hold and relax exercise is shown in FIG. 21, where force 340 is shown as a function of the angle 342, and data for the elbow 344 and forearm 346 are displayed individually.

PNF exercises are a type of static stretch most commonly characterized by a precontraction of the muscle to be stretched and a contraction of the antagonist muscle during the stretch. A PNF exercise according to the teaching of the present invention may be continuous motion of both the elbow and the forearm throughout a predefined range of motion at a predefined velocity, which may or may not vary during the exercise, for a predefined period of time. Rotation about the elbow and forearm axes of rotation during the treatment session may be sequential or simultaneous or a combination of the two. Illustrative, non-limiting examples or data that may be displayed are given in FIG. 22, where, the force is shown as a function of the angle.

The orthotic system of the present invention may be configured for clinical use whereby all of the elements of the system ire located in the clinic. Alternatively, the external actuating device 2 and the remote control unit 500 may be supplied with computer software for remote communication to the clinic computer, whereby they will be configured for attachment to a home computer. In such a situation, real time control of the device will be monitored by the home computer, or on-board microprocessor and data will be transferred to the clinic computer via internet, or by direct telephone connection, for review by a doctor or therapist, at which time operational parameters may be reset to new values. A further alternative may circumvent the home computer and provide for direct connection to the clinic computer via telephone lines. In such a case, all of the operational parameters of the device would be controlled by the clinic computer, as would data collection and analysis. That is, the external actuating device will need to be plugged in to a telephone jack during treatment sessions.

It will be appreciated by one of ordinary skill in the art that the operational features, and data collection and analysis capabilities of an orthotic system according to the teachings of the present invention may be readily adapted for use in an assistive orthotic device. Such an assistive system may include a microchip to control real time operational parameters of the device, and supply a data link for connection to a computer for parameter review and adjustment. The remote control unit may be configured so as to be worn by the patient. Alternatively, the hydraulic system may be configured such that the external actuating device is self-contained. The operational regimen described above with regard to active range of motion assessment mode may be one non-limiting example of an assistive operational regimen for an orthotic system constructed and operative according to the principles of the present invention.

It will be appreciated that the above descriptions are intended only to serve as examples, and that many other embodiments are possible within the spirit and the scope of the present invention.

What is claimed is:

1. A method for self-adaptive motion treatment of a jointed body part of a patient, said jointed body part having at least three rotatable body sections interconnected by at least two joints, the method comprising:
   a) attaching an external actuating device physically to said jointed body part, said device including at least one actuator for applying force to generate or oppose movement of said jointed body part; at least one sensor arrangement for sensing a force generated by said jointed body part relative to said external actuating device; and, at least one sensor arrangement for sensing the position of said jointed body part; such that first axis of device rotation, which is an axis about which said body sections rotate in relation to each other, is placed upon said first axis of body-part-rotation; and at least a second axis of device rotation is placed upon at least a second axis of body-part-rotation;
   b) activating said external actuating device during repeated performance of set of a motions including rotating the body parts about said axes of body part rotation so as to interact with said jointed body part according to a certain set of treatment parameters;
   c) during repetitions of said set of motions, collecting and storing data relating to the force generated by the jointed body part relative to said external actuating device and to the position of the jointed body part;
   d) analyzing said data by use of a data processor according to a predefined set of analysis rules; and,
   during said activating, modifying, responsive to said data analysis, at least one parameter of said set of treatment parameters during an uninterrupted treatment session, thereby modifying the interaction of said external actuating device with said jointed body part during at least one repetition of said set of motions based at least in part on data collected during previous repetitions of said set of motions.

2. The method of claim 1, wherein said rotating of said sections about said axis of device-rotation is implemented as rotation about said first and second axes of device-rotation, and said first and second axes of device-rotation are perpendicular to each other.

3. The method of claim 1, wherein said rotating about said first and second axes of device-rotation is implemented as substantially simultaneous rotation about said first and second axes of device-rotation.

4. The method of claim 1, wherein said collecting data includes collecting data regarding angular orientation of each one of said sections in relation to others of said sections.

5. The method of claim 1, wherein said collecting data includes collecting force related data.

6. The method of claim 1, wherein said collecting data includes collecting time related data.

7. The method of claim 1, wherein said parameters include angular movement velocity of at least one of said sections.

8. The method of claim 1, wherein said parameters include force applied by at least one said section to the body part.

9. The method of claim 1, wherein said parameters include time of said activating of said external actuating device.

10. The method of claim 1, wherein said activating further includes using a control unit in electronic communication with said data processor, said control unit further being in control communication with said external actuating device.

11. The method of claim 10, further comprising activating hydraulic actuators associated with said external actuating device to achieve said rotation, said control communication therefore being fluid communication.

12. The method of claim 11, wherein said control unit is implemented as a remote control unit.

13. The method of claim 1, further comprising displaying representations of said data.

14. The method of claim 13, wherein said displaying is implemented as a substantially continuous, real time display of said data.

15. The method of claim 1, wherein said certain set of parameters relate to said activating being in a rehabilitative mode.

16. The method of claim 1, wherein said certain set of parameters related to said activating device being in an assistive mode.

17. The method of claim 1, wherein said data collecting includes saving said data for later retrieval.

18. The method of claim 17, wherein said saving includes adding said data to a database.

19. The method of claim 18, wherein said database is implemented as a patient dedicated database.

20. The method of claim 18, wherein said database is implemented as a system database.

21. The method of claim 18, wherein said analysis includes analysis of data in said database.

22. The method of claim 21, wherein said analysis includes comparison of data from a current session from at least one previous session.

23. The method of claim 21, wherein said analysis includes comparison of data from a current session to data in said database.

24. The method of claim 21, wherein said analysis includes analysis of rehabilitative progress.

25. The method of claim 21, wherein said analysis is included in a decision making process of a treatment team.

26. The method for self-adaptive treatment according to claim 1, wherein said external actuating device includes at least one actuator for applying force to oppose movement of the jointed body part.

27. A system for treating self-adaptive treatment of a jointed body part of a patient, said jointed body part having at least three rotatable body sections interconnected by at least two joints, the system comprising:
   a) means for attaching an external actuating device physically to said jointed body part, said device including at least one actuator for applying force to generate or oppose movement of said jointed body part; at least one sensor arrangement for sensing a force generated by said jointed body part relative to said external actuating device; and, at least one sensor arrangement for sensing the position of said jointed body part; such that first axis of device rotation, which is an axis about which said body sections rotate in relation to each other, is placed upon said first axis of body-part-rotation; and at least a second axis of device rotation is placed upon at least a second axis of body-part-rotation;
   b) means for activating said external actuating device during repeated performance of set of a motions including rotating the body parts about said axes of body part rotation so as to interact with said jointed body part according to a certain set of treatment parameters;
   c) means for repetitively collecting and storing data relating to the force generated by said jointed body part relative to said external actuating device and to the position of the jointed body part;
   d) means for analyzing said data by use of a data processor according to a predefined set of analysis rules; and,
   e) means for modifying, responsive to said data analysis, at least one parameter of said set of treatment parameters during activating an uninterrupted treatment session, thereby modifying the interaction of said external actuating device with said jointed body part during at least one repetition of said set of motions based at least in part on data collected during previous repetitions of said set of motions.

28. The system of claim 27, wherein said first and second axes of device-rotation are perpendicular to each other.

29. The system of claim 28, wherein said rotating about said two axes of device-rotation is implemented as substantially simultaneous rotation about said two axes of device-rotation.

30. The system of claim 29, wherein said data collecting elements include elements configured to collect data regarding angular orientation of each one of said sections in relation to others of said sections.

31. The system of claim 27, wherein said data collection elements include elements configured to collect force related data.

32. The system of claim 27, wherein said data collection elements include elements configured to collect time related data.

33. The system of claim 27, wherein said data collection elements include a tension/compression load cell.

34. The system of claim 27, wherein said data collection elements include an encoder.

35. The system of claim 27, wherein said data collection elements include a torque sensor.

36. The system of claim 27, wherein said certain set of parameters includes angular velocity of at least one of said sections.

37. The system of claim 27, wherein said certain set of parameters includes force exerted by at least one of said sections.

38. The system of claim 27, wherein said certain set of parameters includes time during which said external actuating device is activated.

39. The system of claim 27, further comprising a control unit in electronic communication with said data processor, and in control communication with said external actuating device.

40. The system of claim 39, further comprising hydraulic actuators associated with said external actuating device, said hydraulic actuators configured so as to rotate said sections about said axis device-rotation, said control communication therefore being fluid communication.

41. The system of claim 40, wherein said data collection elements include a fluid pressure sensor.

42. The system of claim 41, wherein said control unit is implemented as a remote control unit.

43. The system of claim 27, wherein said data processor includes a display component configured to display representation of said data.

44. The system of claim 43, wherein said data processor is configured such that said display of data representations is a substantially continuous, real time display of said data.

45. The system of claim 27, wherein said data is saved for later retrieval.

46. The system of claim 45, wherein said data is added to a database.

47. The system of claim 46, wherein said database is implemented as a patient dedicated database.

48. The system of claim 46, wherein said database is implemented as a system database.

49. The system of claim 46, wherein said data processor analyzes said data in said database.

50. The system of claim 49, wherein said data processor is configured to compare data from a current session to data from at least one previous session.

51. The system of claim 49, wherein said data processor is configured to compare data from a current session to data in said database.

52. The system of claim 49, wherein said data processor is configured to analyze rehabilitative progress.

53. The system of claim 49, wherein said data processor is configured to provide data to aid a decision making process of a treatment team.

54. The system for self-adaptive treatment according to claim 27, wherein said external actuating device includes at least one actuator for applying force to oppose movement of the jointed body part.

* * * * *